(12) United States Patent
Marquez Chin et al.

(10) Patent No.: US 10,194,858 B2
(45) Date of Patent: Feb. 5, 2019

(54) METHOD AND SYSTEM FOR BRAIN ACTIVITY SIGNAL-BASED TREATMENT AND/OR CONTROL OF USER DEVICES

(71) Applicant: UNIVERSITY HEALTH NETWORK, Toronto (CA)

(72) Inventors: César Marquez Chin, Toronto (CA); Kathryn Atwell, Etobicoke (CA); Milos R. Popovic, Mississauga (CA)

(73) Assignee: UNIVERSITY HEALTH NETWORK (CA)

( * ) Notice: Subject to any disclaimer, the term of this patent is extended or adjusted under 35 U.S.C. 154(b) by 0 days.

(21) Appl. No.: 15/450,839

(22) Filed: Mar. 6, 2017

(65) Prior Publication Data

US 2017/0172497 A1   Jun. 22, 2017

Related U.S. Application Data

(63) Continuation-in-part of application No. PCT/CA2015/050839, filed on Sep. 2, 2015.

(Continued)

(51) Int. Cl.

| | |
|---|---|
| *A61F 2/72* | (2006.01) |
| *A61B 5/00* | (2006.01) |
| *A61B 5/0478* | (2006.01) |
| *A61N 1/36* | (2006.01) |
| *A61B 5/04* | (2006.01) |
| *A61B 5/1468* | (2006.01) |

(Continued)

(52) U.S. Cl.
CPC ........ *A61B 5/4851* (2013.01); *A61B 5/04008* (2013.01); *A61B 5/048* (2013.01); *A61B 5/0478* (2013.01); *A61B 5/1468* (2013.01); *A61B 5/4836* (2013.01); *A61B 5/7246* (2013.01); *A61F 2/72* (2013.01); *A61F 5/01* (2013.01); *A61N 1/36003* (2013.01); *G06F 3/015* (2013.01); *A61H 2230/105* (2013.01); *A63B 2230/105* (2013.01)

(58) Field of Classification Search
None
See application file for complete search history.

(56) References Cited

U.S. PATENT DOCUMENTS

| | | |
|---|---|---|
| 7,120,486 B2 | 10/2006 | Leuthardt et al. |
| 2012/0022391 A1 | 1/2012 | Leuthardt |

(Continued)

FOREIGN PATENT DOCUMENTS

| | | | |
|---|---|---|---|
| CN | 102613972 A | * 8/2012 | .......... A61B 5/0476 |
| WO | 2014069996 A1 | 5/2014 | |

OTHER PUBLICATIONS

Liao K, Xiao R, Gonzalez J, Ding L. Decoding individual finger movements from one hand using human EEG signals. PLoS One. Jan. 8, 2014;9(1):e85192.

(Continued)

*Primary Examiner* — David H Willse
(74) *Attorney, Agent, or Firm* — Barnes & Thornburg LLP

(57) ABSTRACT

A method for characterizing a brain electrical signal comprising forming a temporo-spectral decomposition of the signal to form a plurality of time resolved frequency signal values, associating each instance of the signal value with a predetermined function approximating a neurological signal to form a table of coefficients collectively representative of the brain electrical signal.

17 Claims, 12 Drawing Sheets

Related U.S. Application Data

(60) Provisional application No. 62/046,078, filed on Sep. 4, 2014.

(51) Int. Cl.
*A61F 5/01* (2006.01)
*G06F 3/01* (2006.01)
*A61B 5/048* (2006.01)

(56) References Cited

U.S. PATENT DOCUMENTS

2012/0296569 A1 11/2012 Shahaf et al.
2015/0012111 A1 1/2015 Contreras-Vidal et al.

OTHER PUBLICATIONS

Xiao R, Ding L. Evaluation of EEG features in decoding individual finger movements from one hand. Comput Math Methods Med. 2013;2013:243257.
Quandt F, Reichert C, Hinrichs H, Heinze HJ, Knight RT, Rieger JW. Single trial discrimination of individual finger movements on one hand: a combined MEG and EEG study. Neuroimage. Feb. 15, 2012;59(4):3316-24.
Wissel T, Pfeiffer T, Frysch R, Knight RT, Chang EF, Hinrichs H, Rieger JW, Rose G. Hidden Markov model and support vector machine based decoding of finger movements using electrocorticography. J Neural Eng. Oct. 2013;10(5):056020.
Kappeller C, Schneider C, Kamada K, Ogawa H, Kunii N, Ortner R, Pruckl R, Guger C. Single trial detection of hand poses in human ECoG using CSP based feature extraction. Conf Proc IEEE Eng Med Biol Soc. 2014;2014:4599-602.
Chestek, CA, Gilja V. Blabe CH, Foster BL, Shenoy KV, Parvizi J, Henderson JM. Hand posture classification using electrocorticography signals in the gamma band over human sensorimotor brain areas. J. Neural Eng. Apr. 2013,10(2):026002.
Pistohl T, Schulze-Bonhage A, Aertsen A, Mehring C, Ball T. Decoding natural grasp types from human ECoG. Neuroimage. Jan. 2, 2012;59(1):248-60.
Wang W, Degenhart AD, Collinger JL, Vinjamuri R, Sudre GP, Adelson PD, Holder DL, Leuthardt EC, Moran DW, Boninger ML, Schwartz AB, Crammond DJ, Tyler-Kabara EC, Weber DJ. Human motor cortical activity recorded with Micro-ECoG electrodes, during individual finger movements. Conf Proc IEEE Eng Med Biol Soc. 2009;2009:586-9.
Aggarwal V, Acharya S, Tenore F, Shin HC, Etienne-Cummings R, Schieber MH, Thakor NV. Asynchronous decoding of dexterous finger movements using M1 neurons. IEEE Trans Neural Syst Rehabil Eng. Feb. 2008;16(1):3-14.
Milekovic T, Fischer J, Pistohl T, Ruescher J, Schulze-Bonhage A, Aertsen A, Rickert J, Ball T, Mehring C. An online brain-machine interface using decoding of movement direction from the human electrocorticogram. J Neural Eng. Aug. 2012;9(4):046003.
Kubánek J, Miller KJ, Ojemann JG, Wolpaw JR, Schalk G. Decoding flexion of individual fingers using electrocorticographic signals in humans. J Neural Eng. Dec. 2009;6(6):066001.
Ryun S, Kim JS, Lee SH, Jeong S, Kim SP, Chung CK. Movement type prediction before its onset using signals from prefrontal area: an electrocorticography study. Biomed Res Int. 2014;2014:783203.
Wang PT, King CE, McCrimmon CM, Shaw SJ, Millett DE, Liu CY, Chui LA, Nenadic Z, Do AH. Electrocorticogram encoding of upper extremity movement duration. Conf Proc IEEE Eng Med Biol Soc. 2014;2014:1243-6.
Zanos S, Miller KJ, Ojemann JG. Electrocorticographic spectral changes associated with ipsilateral individual finger and whole hand movement. Conf Proc IEEE Eng Med Biol Soc. 2008;2008:5939-42.
Paek AY, Agashe HA, Contreras-Vidal JL. Decoding repetitive finger movements with brain activity acquired via non-invasive electroencephalography. Front Neuroeng. Mar. 13, 2014;7:3.
Pistohl T, Ball T, Schulze-Bonhage A, Aertsen A, Mehring C. Prediction of arm movement trajectories from ECoG-recordings in humans. J Neurosci Methods. Jan. 15, 2008;167(1):105-14. Epub Oct. 10, 2007.
Waldert S, Braun C, Preissl H, Birbaumer N, Aertsen A, Mehring C. Decoding performance for hand movements: EEG vs. MEG. Conf Proc IEEE Eng Med Biol Soc. 2007;2007:5346-8.
Anderson NR, Blakely T, Schalk G, Leuthardt EC, Moran DW. Electrocorticographic (ECoG) correlates of human arm movements. Exp Brain Res. Nov. 2012;223(1):1-10. doi: 10.1007/s00221-012-3226-1. Epub Sep. 22, 2012.
Aggarwal V, Mollazadeh M, Davidson AG, Schieber MH, Thakor NV. State-based decoding of hand and finger kinematics using neuronal ensemble and LFP activity during dexterous reach-to-grasp movements. J Neurophysiol. Jun. 2013;109(12):3067-81.
Agashe, Harshavardhan A., Jose L. Contreras-Vidal; Reconstructing hand kinematics during reach to grasp movements from electroencephalographic signals; 33rd Annual International Conference of the IEEE EMBS, Boston, MA, Aug. 30-Sep. 3, 2011, pp. 5444-5447.
Bradberry TJ, Gentili RJ, Contreras-Vidal JL Reconstructing three-dimensional hand movements from noninvasive electroencephalographic signals. J Neurosci. Mar. 3, 2010;30(9):3432-7.
Miller KJ, Zanos S, Fetz EE, den Nijs M, Ojemann JG. Decoupling the cortical power spectrum reveals real-time representation of individual finger movements in humans. J Neurosci. Mar. 11, 2009;29(10):3132-7.
Zhou J, Yao J, Deng J, Dewald JPA. EEG-based classification for elbow versus shoulder torque intentions involving stroke subjects. Computers in biology and medicine. May 2009;39(5):443-52.
Bai O, Rathi V, Lin P, Huang D, Battapady H, Fei D-Y, et al. Prediction of human voluntary movement before it occurs. Clin Neurophysiol. Feb. 1, 2011;122(2)364-72.
Xiao R, Ding L. Evaluation of EEG Features in Decoding Individual Finger Movements from One Hand. Computational and mathematical methods in medicine. Hindawi Publishing Corporation; 2013;2013.
Supplementary European Search Report for European Patent Application No. EP15838978; dated Mar. 27, 2018.
International Preliminary Report on Patentability and Written Opinion for International Patent Application No. PCT/CA2015/050839; dated Mar. 16, 2017.
Suwannarat et al.; "Comparison of EEG measurement of upper limb movement in motor imagery training system," Biomedical Engineering online 17.1 (2018); 22 pages.
Savic A. et al.; "11. Motor imagery based BCI for control of FES", Clinical Neurophysiology, vol. 124, No. 7, Jan. 1 2013.
Seungchan Lee et al.; "Review of Wireless Brain-Computer Interface Systems" In: "Brain-Computer Interface Systems—Recent Progress and Future Prospects", Jun. 5, 2013 (Jun. 5, 2013), InTech.
Pfurtscheller G et al.; "Evaluation of event-related desynchronization (ERD) preceding and following voluntary self-paced movement", Electroencephalography and Clinical Neurophysiology, Elsevier, Amsterdam, NL, vol. 46, No. 2, Feb. 1, 1979 (Feb. 1, 1979), pp. 138-146.

* cited by examiner

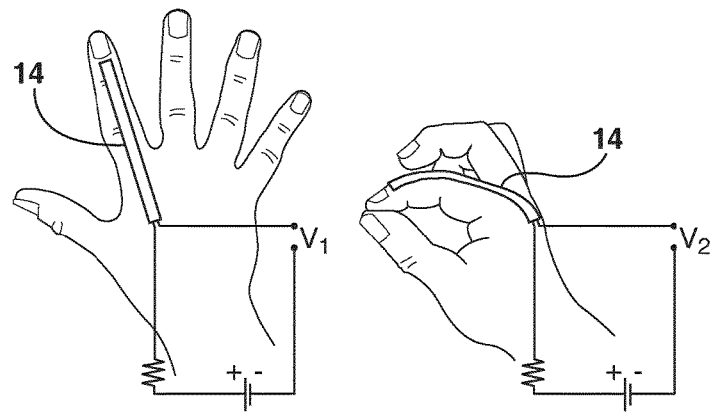
FIG. 3
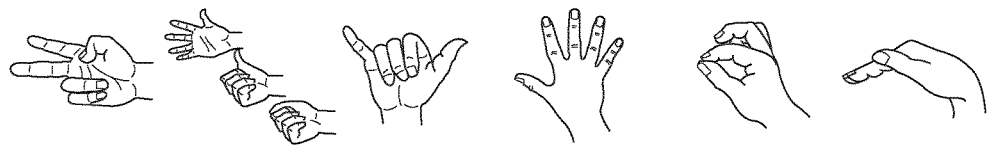
FIG. 4a  FIG. 4b  FIG. 4c  FIG. 4d  FIG. 4e  FIG. 4f
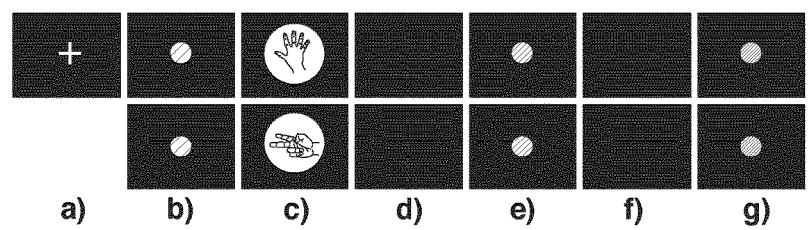
a)   b)   c)   d)   e)   f)   g)
FIG. 5

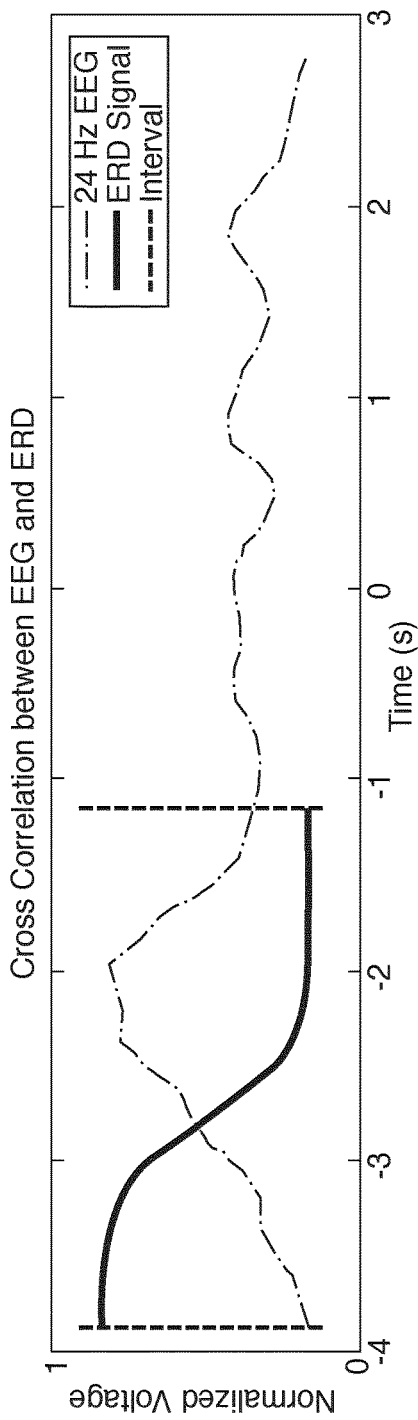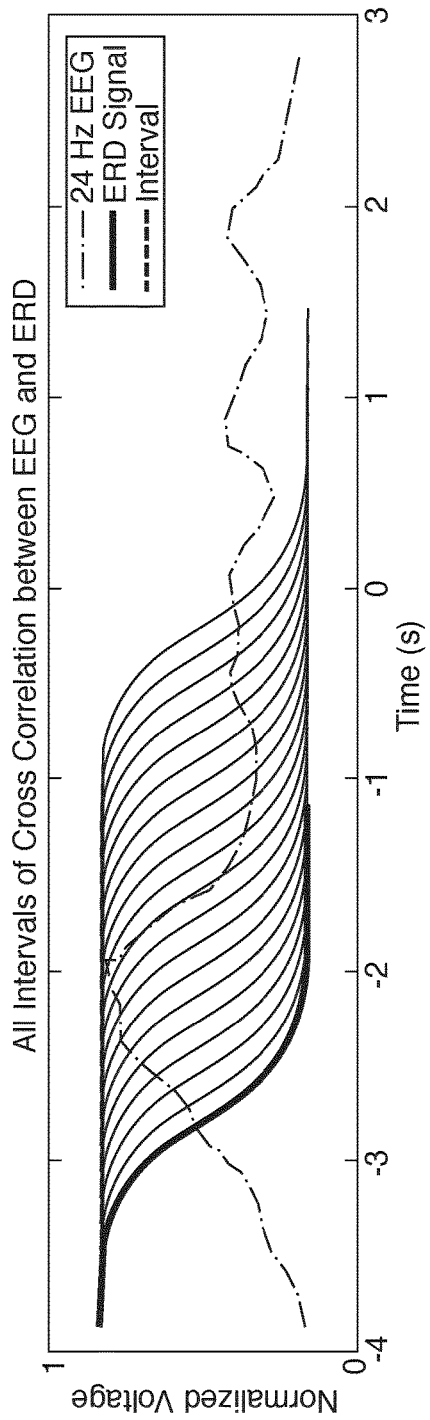
FIG. 10a
FIG. 10b

METHOD AND SYSTEM FOR BRAIN ACTIVITY SIGNAL-BASED TREATMENT AND/OR CONTROL OF USER DEVICES

REFERENCE TO CO-PENDING APPLICATIONS

The entire subject matter of U.S. Provisional application 62/046,078, filed Sep. 4, 2014, entitled METHOD AND SYSTEM FOR IMPROVED BRAIN ACTIVITY SIGNAL ANALYSIS, and PCT application PCT/CA2015/050839 filed Sep. 2, 2015 entitled METHOD AND SYSTEM FOR BRAIN ACTIVITY SIGNAL-BASED TREATMENT AND/OR CONTROL OF USER DEVICES is incorporated herein by reference including materials originally submitted to the U.S. Patent Office.

FIELD OF THE INVENTION

The present invention relates to user treatments or controlling user devices, based on analysis of brain activity signals.

DESCRIPTION OF THE RELATED ART

Current statistics indicate that there are more than 7 million people in the United States who have survived a stroke or brain attack and are living with the after-effects. A large number of these survivors are afflicted by severe upper limb paralysis, and some of these severely paralyzed stroke patients will not respond to conventional therapy and will require long-term assistance. Generally, stroke is caused by hemorrhage (in 15% of cases) or occlusion (in 85% of cases) of a blood vessel in the brain; creating a lesion and localized neuronal death. The brain's ability to regenerate or repair a neural structure damaged by stroke is limited, therefore strokes which affect the sensorimotor cortex can cause permanent motor deficits in the side of the body contralateral to the affected cerebral hemisphere, a condition known as hemiplegia. Specifically, 70-85% of individuals are hemiplegic following their first stroke, and 60% will be unable to independently perform simple activities of daily living (i.e., washing, dressing, and toileting) six months after the event. In response to the bleak prognosis facing stroke patients, research has focused on developing different methods of therapy which emphasize neurological recovery.

One such method is physiotherapy which aims to increase a patient's functional ability using strengthening exercises, passive movements, and neuro-developmental approaches; and another method is occupational therapy which is focussed on improving skills relevant to a specific task and/or developing compensatory strategies. However, motor recovery observed with physiotherapy and occupational therapy typically plateaus in the first six months following stroke.

Functional electrical stimulation (FES) therapy is yet another method which has been used successfully to restore both arm and hand function in stroke patients with severe hemiplegia. This intervention requires a therapist to identify the patient's intent to move their paretic or paralyzed limb, and trigger electrical stimulation which facilitates movement of the same affected limb. The combination of the neural activity (i.e. motor planning) with the afferent input from the resulting movement (caused by electrical stimulation) appears to facilitate positive neuroplastic changes resulting in restoration of voluntary movement. However, reliance on the therapist to determine the patient's intention to move has several drawbacks with respect to FES therapy.

One such drawback is that there is reduced certainty that the patient is actually attempting the movement which is stimulated with FES therapy, or that the patient is actually attempting a movement at all; which makes involvement of the central nervous system uncertain. Another drawback is that the time between the attempt and the delivery of the stimulation, a critical aspect of neuromotor rehabilitation associated with neuroplasticity, may fall outside the latency for optimal recovery, assuming the correct movement was attempted.

Attempts have also been made to develop effective brain computer interfaces to sense a patient's intended action and deploy a prosthetic device to carry out the identified intended action by a patient. However, these attempts have seen limited outcomes.

It is an object of the present invention to mitigate or obviate at least one of the above-mentioned disadvantages.

SUMMARY

In one aspect, there is provided a method for characterizing a brain electrical signal comprising forming a temporo-spectral decomposition of the signal to form a plurality of time resolved frequency signal values, associating each instance of the signal value with a predetermined function approximating a neurological signal to form a table of coefficients collectively representative of the brain electrical signal.

In another aspect, there is provided a method for controlling a device based on a recorded intent of a user, the method comprising:
  a. characterizing a brain electrical signal signifying the intent according to the method as defined herein; and
  b. causing the device to perform the action.

In some exemplary embodiments, the device may be one of a robotic arm or device, full limb prosthesis, partial limb prosthesis, neuroprosthesis or functional electrical stimulation (FES) device that actuates a paralysed limb, and an orthotic device, among others.

In some exemplary embodiments, the causing step may include applying a functional electrical stimulation (FES) treatment (or therapy) to the user to trigger a specific user action, according to the recorded user intent.

In another aspect, there is provided a method of characterizing a brain electrical activity signal emitted during a human activity, comprising forming a plurality of frequency delineated signal segments, and for each signal segment correlating an instance thereof with a function approximating a neuro signal associated with a neurocognitive or neuromuscular (or neurological) activity to form a series correlation values over time, and forming a time versus frequency array of correlation values; and wherein the signal is an electroencephalographic (EEG) or an electrocorticographic (ECoG) signal.

Some exemplary embodiments may include associating a binary one or zero to each of the correlation values according to predetermined criteria.

Some exemplary embodiments may include accumulating a number of arrays, each for an instance of a number of repeated human activities, and establishing an incidence value for each element in the array. The incidence value may be an average value or a probability measure relative to a predetermined array value.

In another aspect, there is provided, in a system, a computer-implemented method for creating numerical and visual representations of brain activities by detecting and analysing transient activity of at least one brain electrical signal, said method having instructions stored in a computer-readable medium and executable by a processing structure to cause said processing structure to at least:

a. form a temporo-spectral decomposition of the signal to form a plurality of time resolved frequency signal values; and b. associate each instance of the signal value to a predetermined function approximating a neurological signal to form a time frequency table of coefficients, the table collectively representative of the signal.

In another aspect, there is provided, in a system, a computer-implemented method for creating numerical and visual representations of brain activities by detecting and analysing transient activity of at least one brain electrical signal, said method comprising instructions stored in a computer-readable medium and executable by a processing structure to cause said processing structure to at least:

a. form a temporo-spectral decomposition of the signal to form a plurality of time resolved frequency signal values;

b. associate each instance of the signal value to a predetermined function approximating a neurological signal to form a time frequency table of coefficients, the table collectively representative of the signal; and c. wherein said brain electrical signal is an electroencephalographic (EEG) or an electrocorticographic (ECoG) signal.

In some exemplary embodiments the brain electrical signal is a pre-motor signal. Further, the the brain electrical signal may be detected and analysed using a brain-computer interface (BCI). The brain-computer interface may comprise an electrode array having electrodes for placement on a subject at predetermined positions.

In some exemplary embodiments, the brain electrical signal comprises data signifying an intended neurocognitive or neuromuscular event. The data may be associated with stored data templates each representative of neuro signals associated with neurocognitive or neuromuscular events to identify the intended neurocognitive or neuromuscular event, respectively.

In some exemplary embodiments, the brain-computer interface is configured to issue a signal output with one or more instructions for an action according to the identified intended neurocognitive or neuromuscular event for execution within a predetermined period.

In some exemplary embodiments, the action may be carried out by a real or virtual device. Examples may include a robotic arm, a full or partial limb prosthesis, or an orthotic device, among others, or an electrically stimulated limb actuable by electrical stimulation.

In another aspect, there is provided a brain-computer interface (BCI), comprising a processing structure configured to at least:

a. receive a brain electrical signal from a subject, the signal including data signifying an intended neurocognitive or neuromuscular event;

b. form a temporo-spectral decomposition of the signal to form a plurality of time resolved frequency signal values;

c. associate the data with stored data templates, each derived from time resolved frequency signal values from template brain electrical signals from the subject and representative of template neurocognitive or neuromuscular events to identify the intended neurocognitive or neuromuscular event; and d. issue a signal output with one or more instructions for an action, according to the identified intended neurocognitive or neuromuscular event, to be executed within a predetermined period of time from the input brain signal.

In another aspect, there is provided a brain-computer interface (BCI), comprising a processing structure configured to at least:

a) receive a first brain electrical signal from a subject, the signal including data signifying a first intended neurocognitive or neuromuscular event;

b) form a temporo-spectral decomposition of the signal to form a plurality of time resolved frequency signal values for the first intended neurocognitive or neuromuscular event;

c) associate the data with stored data templates each derived from time resolved frequency signal values from template brain electrical signals from the subject and representative of template neurocognitive or neuromuscular events to identify the first intended neurocognitive or neuromuscular event; and d) issue a signal output with one or more instructions for an action, according to the identified first intended neurocognitive or neuromuscular event, to be executed within a predetermined period of time from the brain electrical signal;

e) receive a second brain electrical signal from a subject, the signal including data signifying a second intended neurocognitive or neuromuscular event;

f) form a temporo-spectral decomposition of the signal to form a plurality of time resolved frequency signal values for the second intended neurocognitive or neuromuscular event;

g) associate the data with the stored data templates to identify the second intended neurocognitive or neuromuscular event; and h) issue a signal output with one or more instructions for an action, according to the identified second intended neuromuscular event, to be executed within a predetermined period of time from the second brain electrical signal.

In some exemplary embodiments the action may include a neuroprosthesis, a functional electrical stimulation (FES) action, a robotic arm or device action, a prosthetic limb action, or an orthotic device action.

In some exemplary embodiments, the issuing steps are carried out in a pre-motor phase and before a motor phase of a corresponding neurocognitive or neuromuscular event.

In another aspect, there is provided a data template for use with a brain-computer interface (BCI), the data template derived from time resolved frequency signal values from temporo-spectral decompositions of brain electrical signal from a subject representative of a neurocognitive or neuromuscular event to classify an intended neurocognitive or neuromuscular event for an action.

In some exemplary embodiments, the action including a real action or a virtual action. A real action may include a neuroprosthesis, a functional electrical stimulation (FES) action, a robotic arm or device action, a prosthetic limb action, or an orthotic device action.

In some exemplary embodiments the data template may generated by detecting and analysing transient activity of at least one pre-motor brain activity, such as an electroencephalographic (EEG) or an electrocorticographic (ECoG) brain signal. The data template may be stored in a database having a plurality of other data templates, and wherein said database referenced to identify an unclassified brain signal by comparing data associated with said unclassified brain signal to said data templates.

In another aspect, there is provided a method for characterizing a brain activity signal corresponding to an intended activity (IA), comprising recording an event related desynchronization (ERD) signal of the IA, forming a temporo-spectral decomposition of the ERD signal to form a plurality of time resolved frequency ERD signal values, associating each instance of the ERD signal value to a function approximating a synthetic ERD signal to form an ERD table of coefficients collectively representative of the IA.

Some embodiments may include accumulating a number of ERD tables, each for an instance of an IA.

Some embodiments may include forming an ERD signature representation characterizing the IA, from the number of ERD tables for the IA.

Some embodiments may include associating an ERD table for an uncharacterized IA with the ERD signature representation of a characterized IA to determine if the uncharacterized IA is an instance of the characterized IA.

In some exemplary embodiments, the step of recording an ERD signal may include collecting one or more electrode signals from one or more electrodes, with one or more ERD tables being associated with a corresponding electrode signal.

Some exemplary embodiments may further comprise forming the ERD table for a characterized IA from the number of ERD tables for the IA.

Some exemplary embodiments may further comprise forming a comparative ERD table for a plurality of characterized IA's.

Some exemplary embodiments may further comprise recording an ERD signal corresponding to uncharacterized IA and forming an ERD table therefor.

Some exemplary embodiments may further comprise recording the ERD signal corresponding to an uncharacterized IA for a number of successive time values and updating an ERD table for the uncharacterized IA for each time value. The time value may in some cases correspond to overlapping intervals and in other cases to non-overlapping time intervals.

Some exemplary embodiments may further comprise comparing the updated ERD table for the uncharacterized IA with the comparative ERD table to determine if the uncharacterized IA is an instance of one of the characterized IA's.

Some exemplary embodiments may further comprise issuing an identity signal after a minimum number of time values necessary to determine that the uncharacterized IA is an instance one of the characterized IA's.

Some exemplary embodiments may further comprise affirming that the uncharacterized IA is an instance one of the characterized IA's when a predetermined correlation count is achieved, each count corresponding to a correlation between corresponding segments of the ERD tables of the characterized IA's and the uncharacterized IA.

Some exemplary embodiments may further comprise advancing the correlation count when a minimum distance is recorded between corresponding segments of the ERD tables of the characterized IA's and the uncharacterized IA.

Some exemplary embodiments may further comprise comparing an ERD table for an uncharacterized IA with the ERD table for the characterized IA to determine if the uncharacterized IA is an instance of the characterized activity.

In some exemplary embodiments, the issuing of the identity signal occurs before an expiry of a pre-motor phase of an action corresponding to the IA.

Some exemplary embodiments further comprise issuing an action signal in response to the identity signal, to initiate the action corresponding to the IA, and before the expiry of the pre-motor phase of the action corresponding to the IA.

In some exemplary embodiments, the time duration between the action signal and the expiry of the pre-motor phase, is minimized and/or optimized.

In some exemplary embodiments, the brain activity signal may originate from an electrical signal, a magnetic signal, or a chemical signal. In the case of an electrical signal, the brain activity signal may be an electroencephalographic (EEG) or an electrocorticographic (ECoG) signal.

In another aspect, there is provided a method for controlling a user device function based on a recorded ERD signal of a user, the method comprising characterizing an uncharacterized intended activity (IA) as defined herein, and issuing a signal to activate the user device function according to the characterized IA.

In some exemplary embodiments, the user device is one of a robotic arm, full limb prosthesis, partial limb prosthesis, or a user treatment device, a neuroprosthesis or functional electrical stimulation (FES).

In another aspect, there is provided, in a system, a computer-implemented method having instructions stored in a computer-readable medium and executable by a processing structure to cause said processing structure to carry out a method as defined herein.

In another aspect, there is provided a brain-computer interface (BCI), comprising a processing structure configured to at least:
 a. form the ERD table as defined herein; and
 b. issue a signal output for activating a user device function.

In another aspect, there is provided an ERD template for use with a brain-computer interface (BCI), the ERD template formed from one or more ERD tables as defined herein and representative of a plurality of characterized IA's.

In another aspect, there is provided an ERD template, stored on a nontransient computer readable medium, for use with a brain-computer interface (BCI), the ERD template formed from one or more ERD tables as defined herein, and representative of a plurality of characterized IA's.

In another aspect, there is provided an ERD template for use with a brain-computer interface (BCI), the ERD template formed from one or more ERD tables as defined herein, and representative of a neurocognitive or neuromuscular event to classify an intended neurocognitive or neuromuscular event.

Some exemplary embodiments of the above-noted methods and systems may be used to classify brain activity signals, such as electroencephalographic signals, according to specific behaviours using a BCI. For example, a set of templates can be generated by repeating the above-noted method steps over several trials pertaining to the specific behaviour and accumulating the results of all trials in a single histogram. A set of templates is generated for each one of the behaviours to be classified. It is also possible to compare the magnitude of the elements in the histogram against a predetemined threshold and keep only those which exceed the threshold either in their actual magnitudes or normalized values. In order to classify a new electroencephalographic signal the above-noted steps are applied, and for a distance based classifier, the distance (Euclidean or any other suitable definition) is measured between the correlation histogram (for the data to classify) and each one of the correlation matrices for each one of the explored behaviours.

Advantageously, in some exemplary embodiments, the incorporation of a BCI into applications such as FES therapy in which a combined BCI and FES platform that derives a control signal from a non-affected, ipsilateral hemisphere may provide an alternate route of recovery for hemiplegic patients with abnormal or non-existent contralateral neurological activity. In some exemplary embodiments involving FES, a BCI able to classify EEG signals allows for the movement produced by FES to be consistent with the patient's motor intent. In addition, FES may be triggered automatically by the BCI within a specified inter-stimulus interval, improving the therapy's compliance with the conditions required for paired associative stimulation dependent plasticity which governs long-term potentiation (LTP) changes in the motor cortex. As an example, a BCI and FES platform for stroke patients may be able to navigate abnormal neurological activity that can result from a lesion. Therefore, a BCI controlled by ipsilateral (non-lesioned) motor signals, if paired with FES therapy, may provide a solution for patients with deficits in their contralateral neural activity.

In another aspect, there is provided a system for enabling a user device, comprising at least one processor configured to run at least one computer program:
a) to record an event-related desynchronization (ERD) signal received from an input in communication with a challenged user, the ERD signal corresponding to an uncharacterized intended activity (IA) of the user for a each time value of one or more successive time values,
b) for each time value:
  i. to access a comparative ERD table of coefficients for a plurality of characterized IA's, and formed by normalizing correlating a plurality of time resolved frequency ERD signal values with a function approximating a synthetic ERD signal;
  ii. to compare the updated ERD table for the uncharacterized IA with the comparative ERD table to determine if the uncharacterized IA is an instance of one of the characterized IA's; and
c) to issue an identity signal to activate the user device, after a minimum number of time values necessary to determine that the uncharacterized IA is an instance one of the characterized IA's.

In some exemplary embodiments, the program is adapted to issue the identity signal when a predetermined correlation count is achieved, each count corresponding to a correlation between corresponding segments of the ERD tables of the characterized IA's and the uncharacterized IA.

In some exemplary embodiments, the program is adapted to advance the correlation count when a minimum distance is recorded between corresponding segments of the ERD tables of the characterized IA's and the uncharacterized IA.

In some exemplary embodiments, the program is adapted to issue the identity signal before an expiry of a pre-motor phase of an action corresponding to the IA.

In some exemplary embodiments, the program is adapted to initiate the action corresponding to the IA, and before the expiry of the pre-motor phase of the action corresponding to the IA.

In some exemplary embodiments, the brain activity signal originates from an electrical signal, a magnetic signal, or a chemical signal.

In some exemplary embodiments, the brain activity signal is an electroencephalographic (EEG) or an electrocorticographic (ECoG) signal.

In some exemplary embodiments, the processor is adapted to receive the brain activity signal from a plurality of operatively positioned electrodes.

In some exemplary embodiments, the processor is adapted to receive the brain activity signal from a single operatively positioned electrode.

In another aspect, there is provided a system for translating analog event-related desynchronization (ERD) signals from a user into an identifiable intended activity (IA), the system comprising:
a) at least one input to receive one or more ERD signals;
b) at least one output to send device action instructions to a user device to carry out a device action corresponding to the IA; and
c) a controller to communicate with the at least one input and the at least one output of the user device, the controller including at least one special purpose processor configured to run at least one computer program:
  i. to record an ERD signal received from the at least one input, the ERD signal corresponding to an uncharacterized IA of the user for each time value of one or more successive time values,
  ii. for each time value:
    1. to access one or more ERD templates of coefficients for one or more characterized IA's, the ERD templates of coefficients being formed by correlating a plurality of time resolved frequency ERD signal values with a function approximating a synthetic ERD signal;
    2. to update an ERD table for the uncharacterized IA and to compare the updated ERD table with the ERD templates to determine whether the uncharacterized IA is an instance of one of the characterized IA's; and
  iii. to initiate a corresponding device action instruction on at the at least one output after a minimum number of time values necessary to determine whether the uncharacterized IA is an instance one of the characterized IA's.

In some exemplary embodiments, the at least one computer program is configured to identify the IA in response to achievement of a predetermined correlation count, wherein each count corresponds to a correlation between corresponding segments of the ERD templates of the characterized IA's and the updated ERD table of the uncharacterized IA.

In some exemplary embodiments, the at least one computer program is configured to advance the correlation count in response to a minimum distance being recorded between corresponding segments of the ERD templates and updated ERD table of the characterized IA's and the uncharacterized IA respectively.

Some exemplary embodiments further comprise the user device, wherein the user device includes a robotic arm or device, a full or partial limb prosthesis, an orthotic device, an electrical stimulation device, or an interface to a virtual device.

In some exemplary embodiments, the at least one computer program is configured to initiate the device action instruction before the expiry of a pre-motor phase of a user action corresponding to the IA.

In some exemplary embodiments, the ERD signal is an electroencephalographic (EEG) or an electrocorticographic (ECoG) signal, a magnetic signal, or a chemical signal.

In some exemplary embodiments, the at least one input includes a single electrode.

A method for translating analog event-related desynchronization (ERD) signals from a user into an identifiable intended activity (IA) to form one or more ERD templates for use in associating an updated ERD table of an uncharacterized IA therewith to identify and initiate a corresponding intended device action by a user device, the method comprising:
a) recording one or more ERD signals from one or more electrodes operatively placed on the user, wherein each of the ERD signals corresponds to a characterized intended activity (IA) of the user for each time value of one or more successive time values;
b) for each time value, forming a temporo-spectral decomposition of the ERD signal, to form a plurality of time resolved frequency ERD signal values;
c) associating each ERD signal value with a function approximating a synthetic ERD signal to form at least one ERD table of coefficients collectively representative of the characterized IA;
d) repeating step c for a number of instances of the characterized IA to form a number of at least one ERD tables; and
e) forming the ERD template for the characterized IA from the number of ERD tables for the characterized IA.

In some exemplary embodiments, the recording of the one or more ERD signals includes collecting one or more electrode signals from one or more electrodes, with one or more of the ERD tables being associated with a corresponding electrode signal.

In some exemplary embodiments, the time values correspond to overlapping or non-overlapping time intervals.

Some exemplary embodiments further comprise:
a) recording the ERD signal corresponding to an uncharacterized IA for a number of successive time values and updating an ERD table for the uncharacterized IA for each time value; and
b) associating the updated ERD table for the uncharacterized IA with the ERD template of the characterized IA to determine whether the uncharacterized IA is an instance of the characterized IA.

Some exemplary embodiments further comprise issuing a device action instruction after a minimum number of time values necessary to determine whether the uncharacterized IA is an instance of the characterized IA.

Some exemplary embodiments further comprise affirming that the uncharacterized IA is an instance one of the characterized IA's in response to achievement of a predetermined correlation count, wherein each count corresponding to a correlation between corresponding segments of the updated ERD table of the uncharacterized IA and the ERD template of the characterized IA.

Some exemplary embodiments further comprise advancing the correlation count in response to a minimum distance being recorded between corresponding segments of the updated ERD table and the ERD template.

In some exemplary embodiments, the device action instruction occurs before an expiry of a pre-motor phase of an action corresponding to the affirmed IA.

In some exemplary embodiments, the time duration between the device action instruction and the expiry of the pre-motor phase, is minimized and/or optimized.

In some exemplary embodiments, the user device is one of a robotic arm or device, full limb prosthesis, partial limb prosthesis, or a user treatment device, a neuroprosthesis or functional electrical stimulation (FES) device that actuates a paralyzed limb, an orthotic device, or a virtual activity device.

BRIEF DESCRIPTION OF THE DRAWINGS

Several exemplary embodiments of the present invention will now be described, by way of example only, with reference to the appended drawings in which:

FIG. 3 shows a sensor glove indicating a change in output voltage at the onset of movement;
FIGS. 4a, 4b, 4c, 4d, 4e and 4f show six different hand movements;
FIG. 5 is an illustration of the sequence of visual cues;
FIG. 6b shows an optical sensor output from the trail performance of FIG. 6a;
FIG. 6c shows a sensor glove output during the trial performance of FIG. 6a.
FIGS. 10a and 10b are exemplary plots of the cross-correlation between a 24 Hz EEG spectral component of a pinch grasp movement trial and a synthetic ERD signal.

DETAILED DESCRIPTION OF EXEMPLARY EMBODIMENTS

Figure 1:
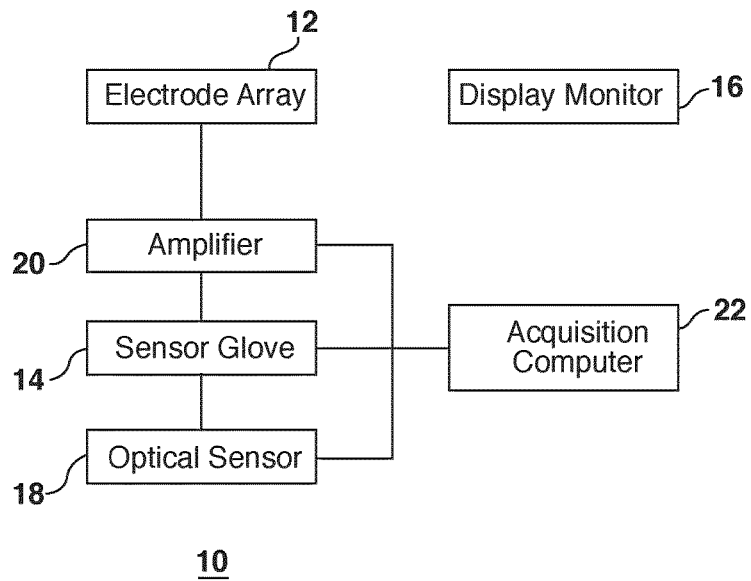
FIG. 1 is a top-level component architecture diagram of an exemplary system for processing brain activity signals.

The detailed description of exemplary embodiments of the invention herein makes reference to the accompanying block diagrams and schematic diagrams, which show the exemplary embodiment by way of illustration and its best mode. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented.

Moreover, it should be appreciated that the particular implementations shown and described herein are illustrative of the invention and its best mode and are not intended to otherwise limit the scope of the present invention in any way. Indeed, for the sake of brevity, certain sub-components of the individual operating components, conventional data networking, application development and other functional aspects of the systems may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

DEFINITIONS

To facilitate understanding of the disclosure, certain terms as used herein are defined below. As used interchangeably herein, the terms "Functional Electrical Stimulation therapy" and "FES therapy" refer to the application of electrical stimulation by a therapist, transcutaneously, to a paretic limb during the patient's conscious effort to move the limb. Examples of FES systems are described in PCT application PCT/CA2011/000637 entitled FUNCTIONAL ELECTRICAL STIMULATION DEVICE AND SYSTEM, AND USE THEREOF, the entire contents and subject matter of which are incorporated herein by reference.

As used herein, the term "brain activity" and "brain activity signal" refer to recordable signals generated by the brain, which may be recorded by way of electrodes or other sensors including those capable of sensing magnetic or chemical activity. Examples of brain activity signals include brain electrical signals including electroencephalography (EEG), and electrocorticography (ECoG) recorded invasively with subdural and/or epidural electrodes and the like.

As used interchangeably herein, the terms "brain-computer interface" and "BCI" refer to a platform which allows its operators to control a peripheral electronic device with activity of the brain.

As used herein, the term "event-related desynchronization" and "ERD" refers to a power decrease in a brain activity signal, such as an EEG signal (among others), which occurs during motor planning and execution. In the case of an EEG signal event, the ERD typically occurs within the alpha (8-12 Hz) and beta (13-30 Hz) bands, though ERD characteristics may also occur at other frequencies or in other frequency ranges. An "ERD signal" refers to a signal which exhibits a measurable ERD.

As used herein, the term "synthetic ERD signal" refers to a waveform approximating a naturally occurring ERD as defined by a mathematical function.

Figure 2:
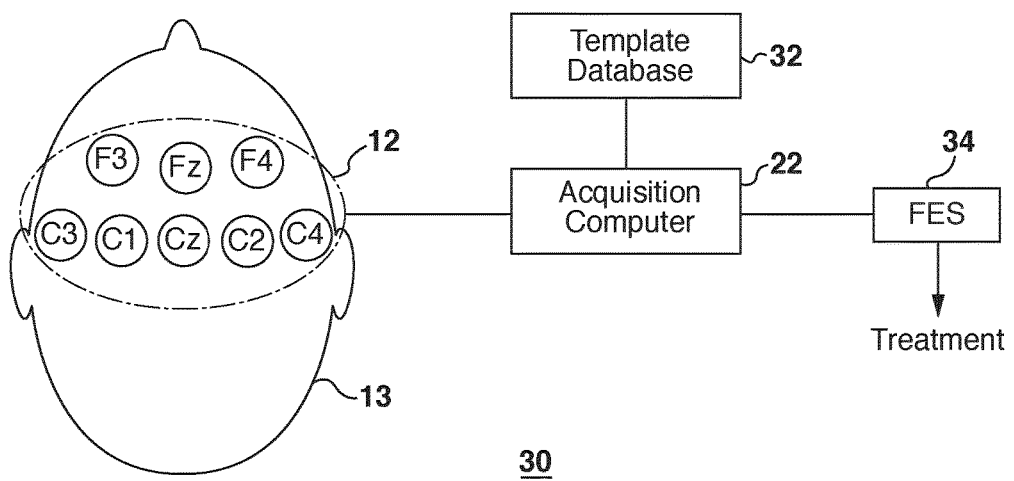
FIG. 2 is top-level component architecture diagram of an exemplary EEG-based BCI and FES system.

FIG. 1 shows a top-level component architecture diagram of an exemplary system, generally identified by reference numeral 10, for detecting and classifying distinct spectral (frequency), temporal (time) or other features of an ERD signal using an EEG-based BCI, though ERD signals may also be in other forms, such as electrocorticography (ECoG) recorded invasively with subdural and/or epidural electrodes. With reference to FIGS. 1 to 3, an ERD signal, in this case in the form of an EEG signal is acquired using an electrode array 12, positioned on a participant's head 13 to sense the brain's activity. A sensor glove 14, worn on the participant's hand, includes a resistive sensor for detecting the onset of a neuromuscular event, in this case resulting in a hand movement. A display monitor 16 presents visual cues to participants, and an optical sensor 18 positioned inconspicuously on display monitor 16 records visual cues to identify the stage of the experiment during data analysis. Signals from both the sensor glove 14 and the optical sensor 18, along with the electrode array 12 are recorded using an amplifier 20, such as the SynAmps RT EEG amplifier, available from Neuroscan, North Carolina, U.S.A. and provided as an input into acquisition computer 22 employing at least one application program, such as CURRY 7 acquisition software, available from Neuroscan, North Carolina, U.S.A. Signals from the sensor glove 14 and optical sensor 18 are also provided as inputs into acquisition computer 22. The signals may be provided to acquisition computer 22 either directly through lead wires or indirectly through a wirelessly transmitted signal. The ERD signals are interpreted and certain features are extracted therefrom using at least one algorithm to generate ERD tables or data templates corresponding to the intended neuromuscular events, which relate to intended activities (IA), such as to include intended firing of muscles and/or muscle groups for movements of parts of the body, such as arms, legs, fingers and toes. The features are classified by correlating them against a function representing a synthetic ERD signal. A main characteristic of the ERD is that it decays or decreases over time, which means that functions operably suited include those which decay or decrease over time, such as nonlinear tangent functions. Other functions, however, may also be used, including linear functions. In a combined BCI and FES system 30, data templates are stored in a template database 32 which is queried by acquisition computer 22 to issue a signal output with one or more instructions to FES system 34. (The FES system 34 may in other exemplified embodiments be replaced by user devices to perform an action, such as a robotic arm, full limb prosthesis, partial limb prosthesis, an orthotic device, among others.) In the case of an FES treatment, the instructions may cause the participant to perform a specific action, or effect treatment, based on the identified intended neuromuscular event or IA.

An exemplary experimental protocol for a study to classify particular hand movements using pre-motor EEG activity using the apparatus presented above will now be described. In the study, the temporo-spectral representation of the ERD signal, in this case an EEG signal, corresponding to specific movements of a hand were correlated with a function representing a synthetic ERD. A measurable ERD signal may be used to differentiate between states of movement and rest. The power decrease in the ERD signal occurs during motor planning and execution. This change in power occurs most prominently in the central region of the brain and is therefore thought to be related to the activity of the sensorimotor cortex. Given that the hand has one of the largest cortical representations in the sensorimotor map, it provides enhanced EEG signal resolution, which may be used to sense an ERD signal, whose features may be correlated with a representative synthetic ERD function.

Fifteen able-bodied individuals were recruited to participate in the study. Of the fifteen participants, fourteen were right handed and six were female. The average age of the participants was 32 years old. The participants were uniquely identified, and for the purposes of this description the participants will be referred to as participant 1, participant 2, participant 3, up to participant 15.

An electrode array 12 with eight electrodes was placed on the participant's head at the following EEG sites: C1, C2, C3, C4, CZ, F3, F4 and FZ (according to the international 10-20 system of electrode placement), as shown in FIG. 2. All electrode sites, reference (linked ear lobes) and ground (clavicle bone) were prepared with 70% isopropyl alcohol and Nuprep® Skin Prep Gel, available from Weaver and Company, Aurora, Colo., U.S.A., prior to electrode placement with Ten20® Conductive EEG Paste, available from Weaver and Company, Aurora, Colo., U.S.A. The impedance at each EEG site was measured, and preferably the impedance had a value of less than 10 kΩ. Detected signals from the eight EEG electrode array 12 were passed through a high-pass filter and sampled thereafter. In one example, a cut off frequency of 0.15 Hz and sampling frequency of 1 kHz was selected. This sampling frequency was chosen to promote temporal resolution and to the increase number of data points, since the signal analysis method may be applied off-line.

Participants were then asked to don a custom-made sensor glove 14 which detected the onset of hand movement using a resistive sensor. FIG. 3 shows a sensor glove 14 indicating a change in output voltage at the onset of movement. The optical sensor 18 was placed against the lower left corner of the display monitor 16 and used to record visual cues, which were concealed from the participant and used to identify the stage of the experiment during data analysis. As described above, the signals from the eight EEG electrodes were recorded using amplifier 20 and acquisition software running on acquisition computer 22, along with signals from both the sensor glove 14 and optical sensor 18.

At the beginning of the session, participants were given instructions to perform six different hand movements including: non-functional 1 movement (FIG. 4a), palmar grasp (FIG. 4b), non-functional 2 movements (FIG. 4c), finger extension (FIG. 4d), pinch grasp (FIG. 4e), and lumbrical grasp (FIG. 4f). These movements were chosen based on their relevance to post-stroke rehabilitation (i.e., finger extension, pinch grasp, lumbrical and palmar grasps) as well as two non-functional grasps which were intended to provide additional test cases for the study.

In each trial, the participants performed one of the specified six hand movements during a specified time interval. Visual cues presented on display 16, including 'ready', 'go' and 'stop', were used to indicate the stage of the trial to the participants, as shown in FIG. 5, and their meanings were explained to the participants prior to commencing the experiment. (FIG. 5 represents examples of separate activities using the examples of FIGS. 4d and 4a respectively.) For example, at the beginning of each trial, the participants were asked to relax for 10 seconds while focusing on a white fixation cross as shown at FIG. 5a. The purpose of this interval was to allow participants to focus on the experiment and disengage from external or environmental distractions. Following the relaxation interval, the participants were presented with a predetermined sequence of visual cues at predetermined time periods. For example, a yellow circle (represented by hatch markings in FIG. 5b), presented at time 1.0 to 3.5 seconds, indicating to the participants that a hand movement is about to be presented. Next, a picture of the hand movement to be performed (FIG. 5c) was presented at time 3.5 to 5.0 seconds, followed by a black screen (FIG. 5d) presented at time 5.0 to 7.0 seconds. Next, a green circle (represented by hatch markings in FIG. 5e) was presented at time 7.0 to 7.5 seconds, indicating the hand movement to be performed, followed by a black screen (FIG. 5f) presented during the execution of the hand movement at time 7.5 to 9.5 seconds. Finally, a red circle (represented by hatch markings in FIG. 5g) was presented at time 9.5 to 10.0 seconds, indicating to the participant to relax their hand. The sequence was repeated for each prescribed hand movement.

In order to minimize participant fatigue the total experimental time was separated into three 6 minute experiments followed by three 5 minute experiments wherein the six hand movements were presented in a random order. The three longer experiments (6 minute) were completed first since participant fatigue generally increased with the duration of the experiment. Each participant was given the opportunity to rest between each experiment.

The participants completed the hand movements with their self-identified dominant hand, except for four of the participants who repeated the experiment with their non-dominant hand during a separate session. Generally, the EEG data collected during dominant hand movements was expected to contain more distinguishable features for classification, since the dominant hand has a larger sensorimotor representation relative to the non-dominant hand. The data collected from the participants using their non-dominant hand was used to measure the robustness of the signal analysis approach developed for this study. In both scenarios, (the dominant or non-dominant hand experiment), each of the six movements were performed an average of 30 times; this sample size allowed for successful movement classification to be reported within a confidence interval of approximately +/−18% and a confidence level of 95%.

Figure 6A:
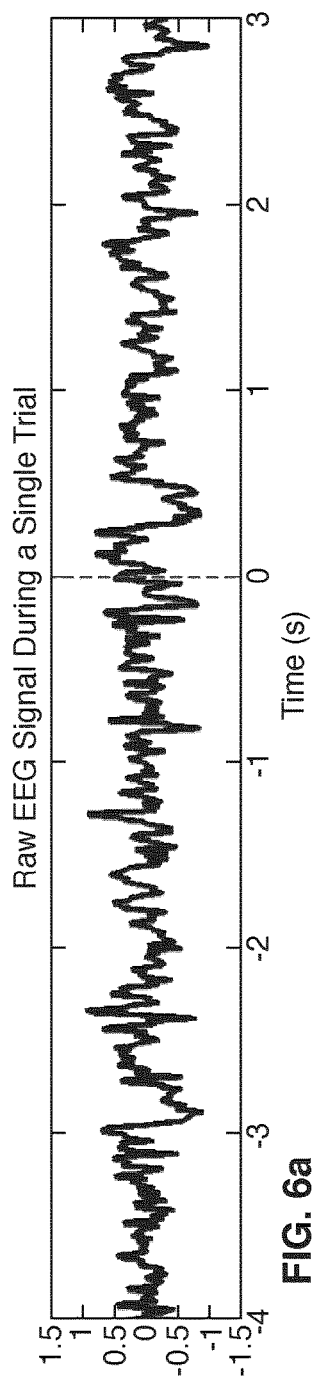
FIG. 6a shows a raw EEG signal during a trial performance of a pinch grasp movement.
Figure 6B:
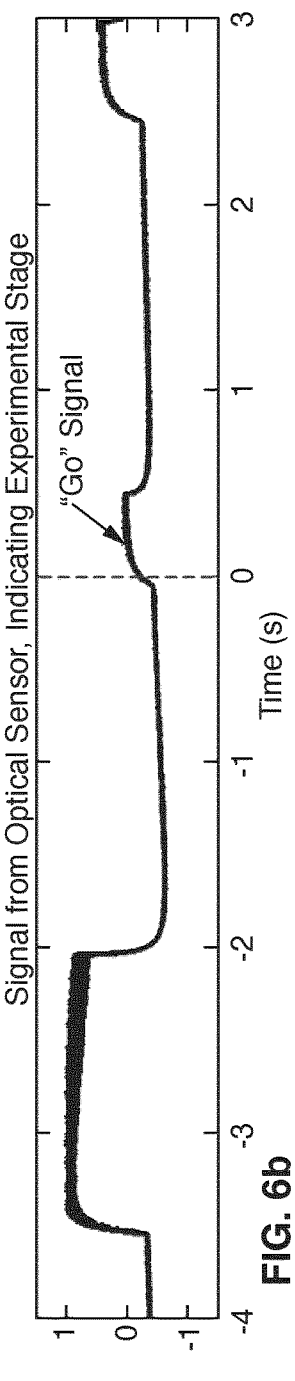
Figure 6C:
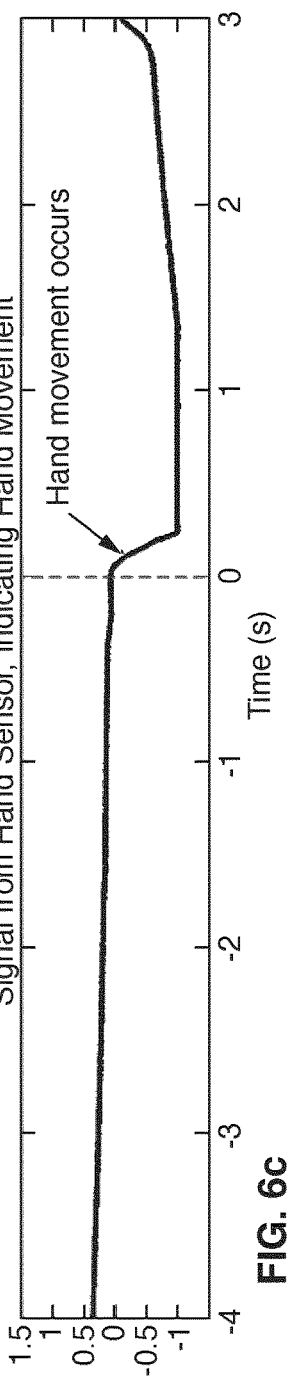

As noted above, signals from the electrode array 12 with the eight EEG electrodes positioned at EEG sites: C1, C2, C3, C4, CZ, F3, F4 and FZ were recorded for each participant as they performed each of the prescribed hand movements. The optical sensor 18 recorded a sequence of visual cues which indicated both the stage of the experiment and the type of hand movement depicted, while the sensor glove 14 detected the type of hand movement. FIG. 6b shows the optical sensor 18 output. FIG. 6c shows sensor glove 14 output during the performance of the pinch. Since each of the six hand movements were distinct, the output of the sensor glove 14 was characteristic to each movement, therefore any trials in which the participant executed the incorrect grasp were identified visually and eliminated from the data. FIG. 6b shows an increase in voltage recorded between −3.5 and −2 seconds corresponding to the time when the participant is viewing the hand movement to be performed. The second voltage increase illustrated in this graph (occurring at approximately 0 seconds) corresponds to the time when the participant receives the instruction to execute the prescribed hand movement (green circle in FIG. 5).

Figure 7:
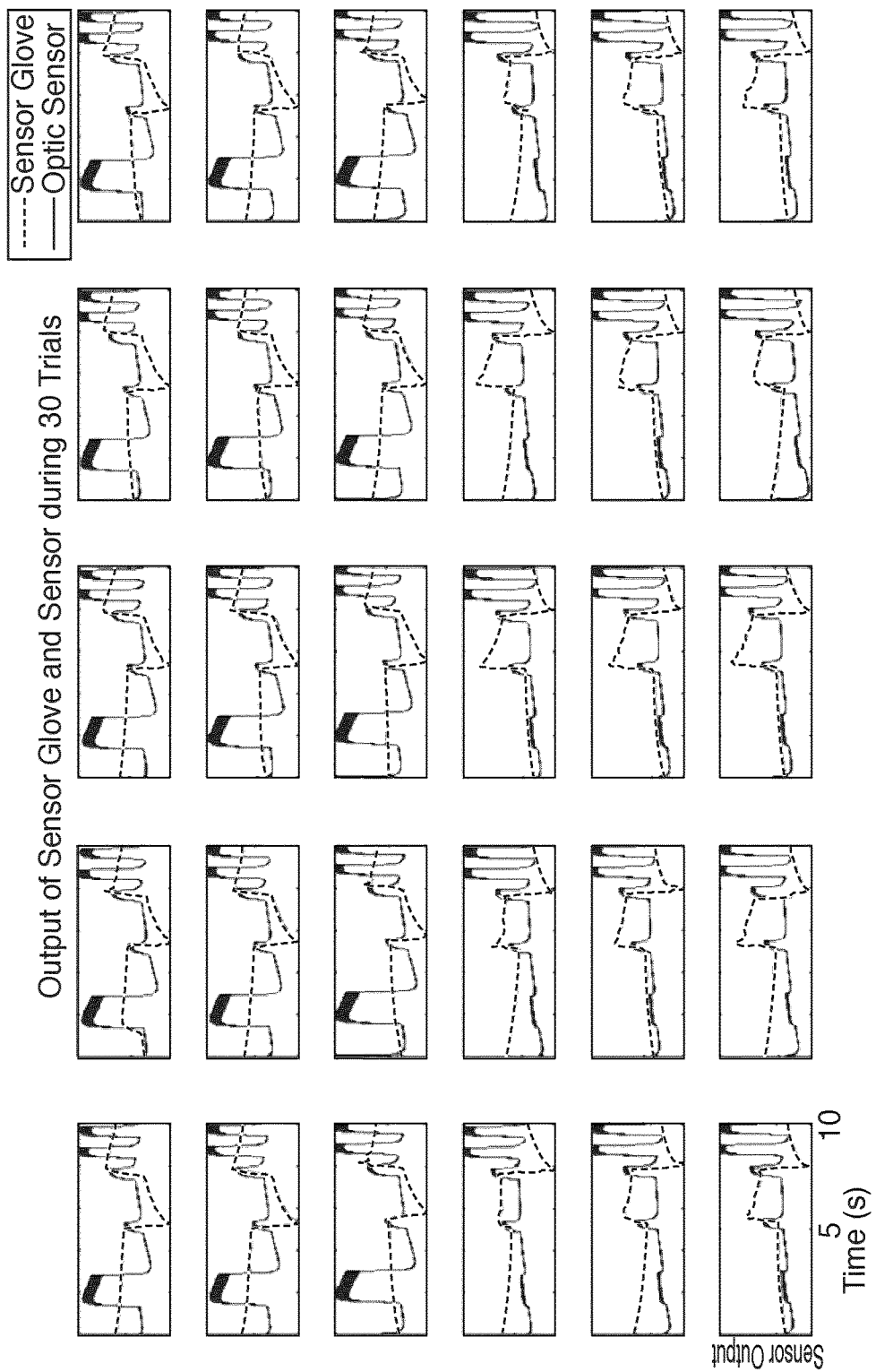
FIG. 7 shows exemplary signals from the sensor glove and the optical sensor recorded by the EEG amplifier before, during, and after executing the pinch grasp and finger extension hand movements.
Figure 8A:
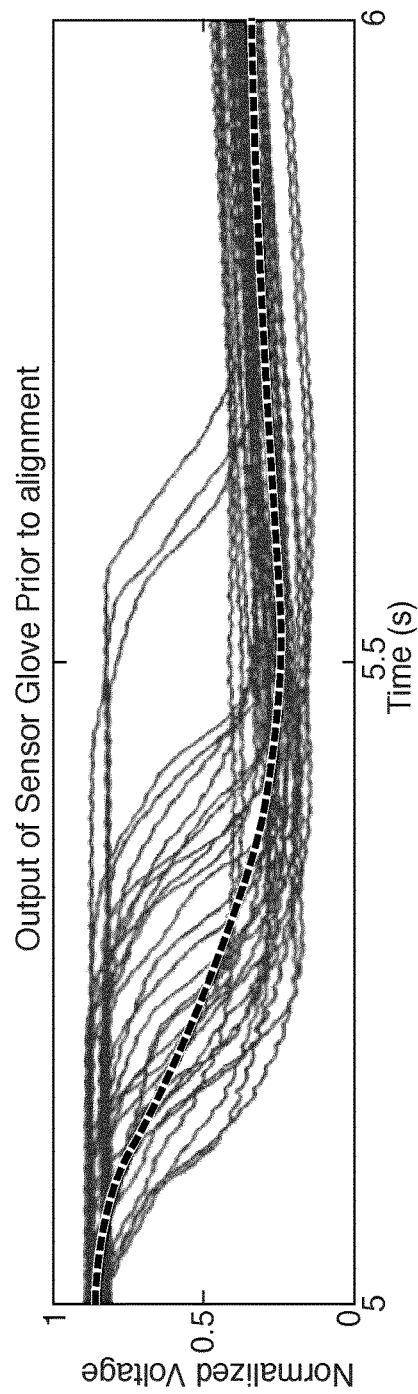
FIG. 8a shows superimposed hand movement data from the sensor glove during a plurality of exemplary trial pinch grasp movements.
Figure 8B:
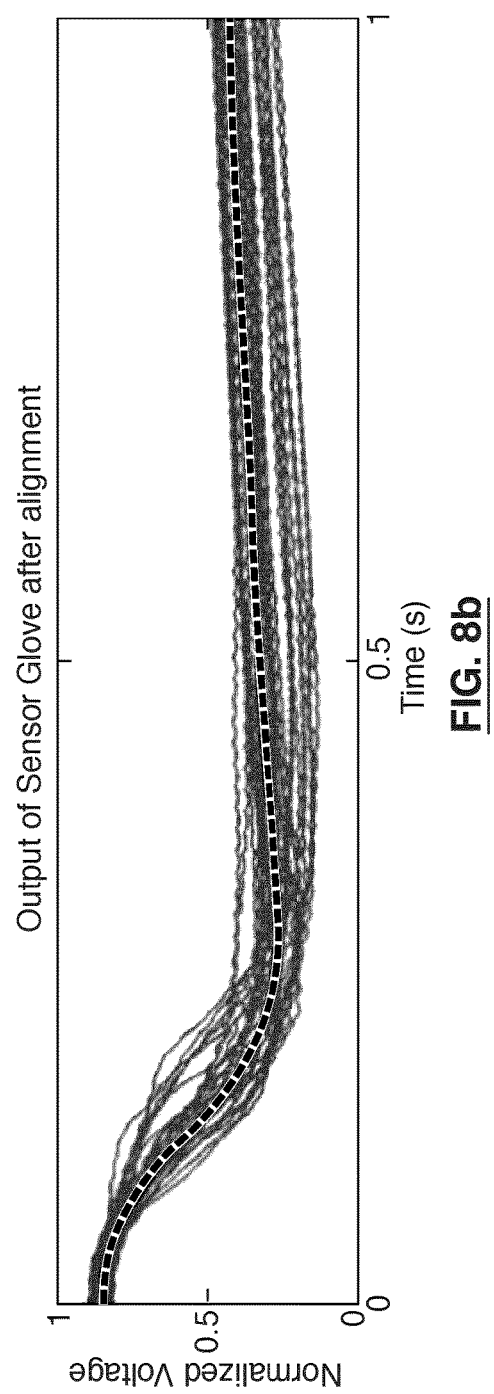
FIG. 8b shows the same superimposed hand movement data from the sensor glove during a plurality of exemplary trial pinch grasp movements shown in FIG. 8a, after alignment with respect to the onset of movement.

FIG. 7 shows exemplary signals recorded by the EEG amplifier 20 during an experiment, before executing the prescribed hand movement and while executing said prescribed hand movement, namely the pinch grasp movement (in rows 1 to 3) and a finger extension hand movement (rows 4 to 6). FIG. 8a shows a graph of the output of the sensor glove 14, where the plots of 30 trials are superimposed (with the dashed line representing average values). FIG. 8b shows the same data after alignment, as discussed below. As can be seen from FIG. 8b, the graph, the onset of hand movement is indicated by the decrease in voltage initiated at 0 seconds. Accordingly, as shown in FIG. 7, it is evident from both the optical sensor 18 output and the sensor glove 14 output that the hand movement was performed shortly after viewing the green circle, as described with reference to FIG. 5, instructing the participant to execute the prescribed hand movement.

The collected EEG data was inputted into a Matlab® application program, available from MathWorks, Natick, Mass., U.S.A., running on acquisition computer 22. The application program included coded instructions to eliminate trials in which the incorrect movement or no movement was performed. As was previously described, the type of movement expected and performed was determined using both the sensor glove 14 and optical sensor 18. Trials in which correct movements were performed were grouped according to the movement and aligned to the onset of movement. FIG. 8a shows hand movement data from the sensor glove 14 worn by the participants during experiment prior to alignment, FIG. 8b shows the same data after alignment. The term "alignment" refers to a process of identifying a specific landmark, in this example a change of voltage in the sensor of sensor glove 14 indicating the onset of movement, and then shifting the signals so that this event is, in each curve, aligned with a common instance of time. This enables the data prior to the landmark to be pre-motor activity for curve analysis purposes, and the data after the landmark to the data after the onset of movement. In this case, this enables the same amount of data to be available for the pre-motor activity, that is prior to the onset of movement. In the example of FIG. 8b, the plots are "aligned" to the landmark defined by the $4^{th}$ second instance of time of the resulting "aligned" signal, which corresponds to the $4000^{th}$ sample. Seven seconds of each trial were extracted for further analysis which included the 4 seconds prior to movement and the 3 seconds following the onset of movement.

Figure 9:
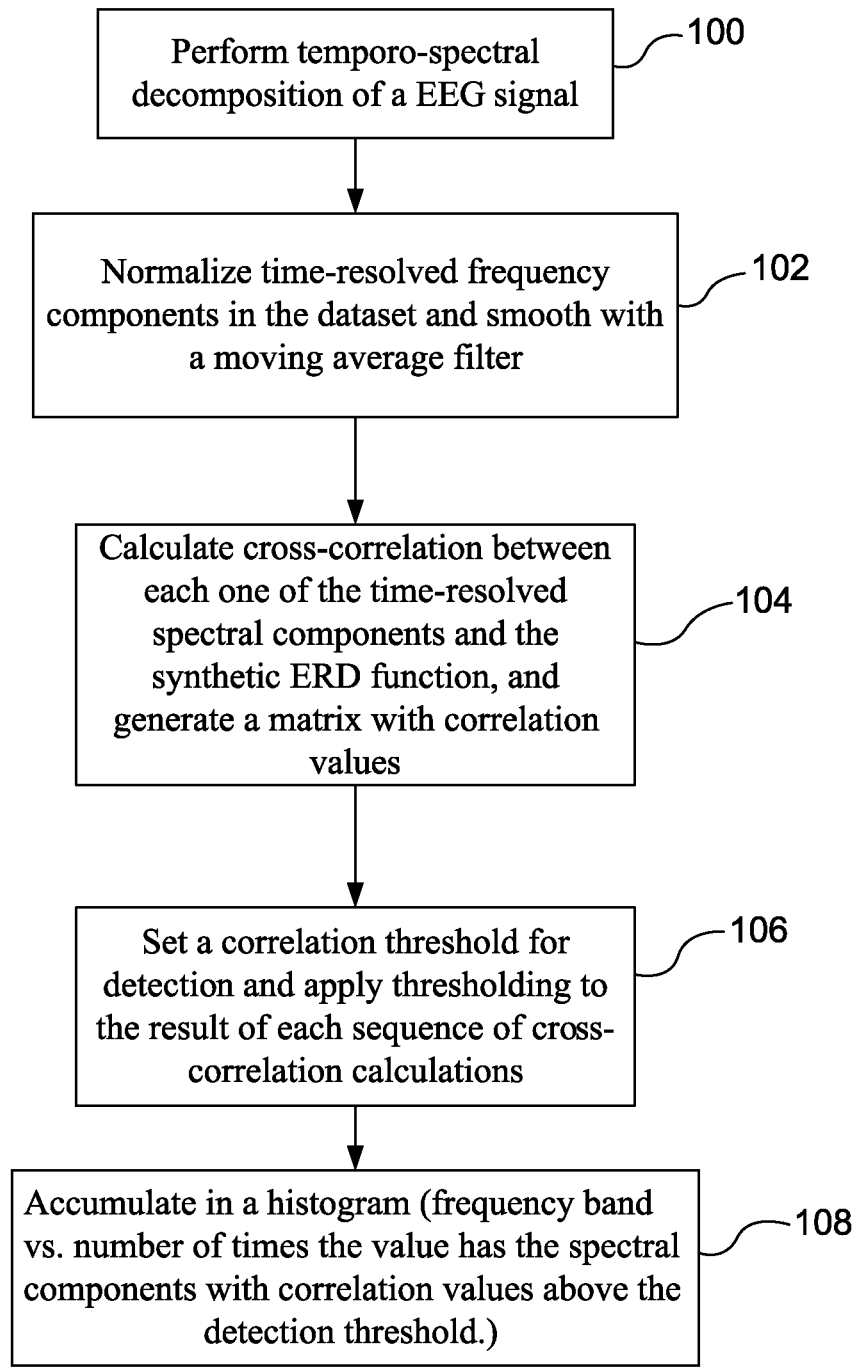
FIG. 9 shows a high level flow diagram illustrating exemplary process steps for classifying an exemplary brain activity signals.

The EEG signal was characterized by following the exemplary method steps shown in a flow chart of FIG. 9.

In step 100, during preliminary analysis of each dataset, temporo-spectral decomposition of each trial was performed using a fast Fourier transform with an exemplary Hamming window of length 256, overlap of 50% and a resolution of 1 Hz for frequencies between 1 and 50 Hz, resulting in a spectrogram (time-frequency) representation of the signal to be analyzed, such as a 72×50 (time-frequency) matrix (spectrogram).

Next, in step 102, each of the time-resolved frequency components (from 1 Hz to 50 Hz) in the dataset was normalized and smoothed using a moving average filter (for example, with a window size of 10).

A synthetic ERD function similar to the general morphology of the naturally occurring ERD event was subsequently determined to provide a synthetic ERD signal, and represented using a hyperbolic tangent function:

$$ERD_{syn} = -(\tan h(4 \times)/3) \quad \text{(Equation 4.1)}$$

Equation 4.1 approximates the general morphology of the naturally occurring ERD event, which is characterized by a power decrease of the EEG within discrete frequency bands of alpha (10-12 Hz) and beta (13-25 Hz) preceding and during voluntary movement.

Next, in step 104, a cross-correlation between each one of the time-resolved spectral components and the synthetic ERD function was calculated, to generate a matrix (spectral components versus time instances) with correlation values. For example, cross-correlation coefficients between each of the time-resolved frequency signals, from 1 to 50 Hz and the synthetic representation of an ERD were determined with the following exemplary equation:

$$R(i, (ERD_{syn}, f_j)) = \frac{C(ERD_{syn}, f_j)}{\sqrt{C(ERD_{syn}, ERD_{syn}) \cdot C(f_j, f_j)}}; \quad \text{(Equation 4.2)}$$

$$j \in [1, 2, \ldots, 50] i \in [1, 2, \ldots, 20]$$

where R refers to a matrix of cross-correlation coefficients between the synthetic ERD signal ($ERD_{syn}$) and a time-resolved frequency signal ($f_j$), where $j \in [1, 2, \ldots, 50]$ for each time instance, $i \in [1, 2, \ldots, 20]$. $C(ERD_{syn}, f_j)$ is the covariance between the two signals, $ERD_{syn}$ and $f_j$; $C(ERD_{syn}, ERD_{syn})$ is the variance of the ERD signal, and $C(f_j, f_j)$ is the variance of a time-resolved spectral component. Equation 4.2 was applied to segments of each time-resolved spectral component, which were 20 data points in length, at 20 instances prior to the onset of movement with an overlap between segments of 19 data points. Each of the times instances, from 1 to 20, corresponds to a time prior to the onset of movement as illustrated in Table 1. For greater clarity, FIGS. 10a and 10b illustrate all of the instances in which the cross-correlation is applied. In this case, the majority of the downward slope of the EEG signal (which actually contains the most information and therefore is most relevant for the detection process) is before the onset of the movement. FIG. 10b shows the application of Equation 4.2 for all 20 time intervals, for a 23 Hz smoothed and normalized time-resolved spectral component (represented in black ink) recorded during a pinch grasp, in which movement onset occurs at 0 seconds. Represented in solid lines are the multiple instances of the synthetic ERD signal where cross-correlation coefficient were calculated.

In step 106, thresholding was applied to the result of each sequence of cross-correlation calculations according to the following criterion:

$$G(i,j,k)_n = 1 \text{ for } R_{i,j} \geq n \text{ and } 0 \text{ for } R_{i,j} < n; i \in [1\ 20], j \in [1\ 50], k = \text{number of trials} \quad \text{(Equation 4.3)}$$

where $G_n$ contains binary values of correlations which exceed a specific threshold: n=[0.6, 0.65, 0.7, 0.75, 0.8, 0.85, 0.9].

Figure 11:
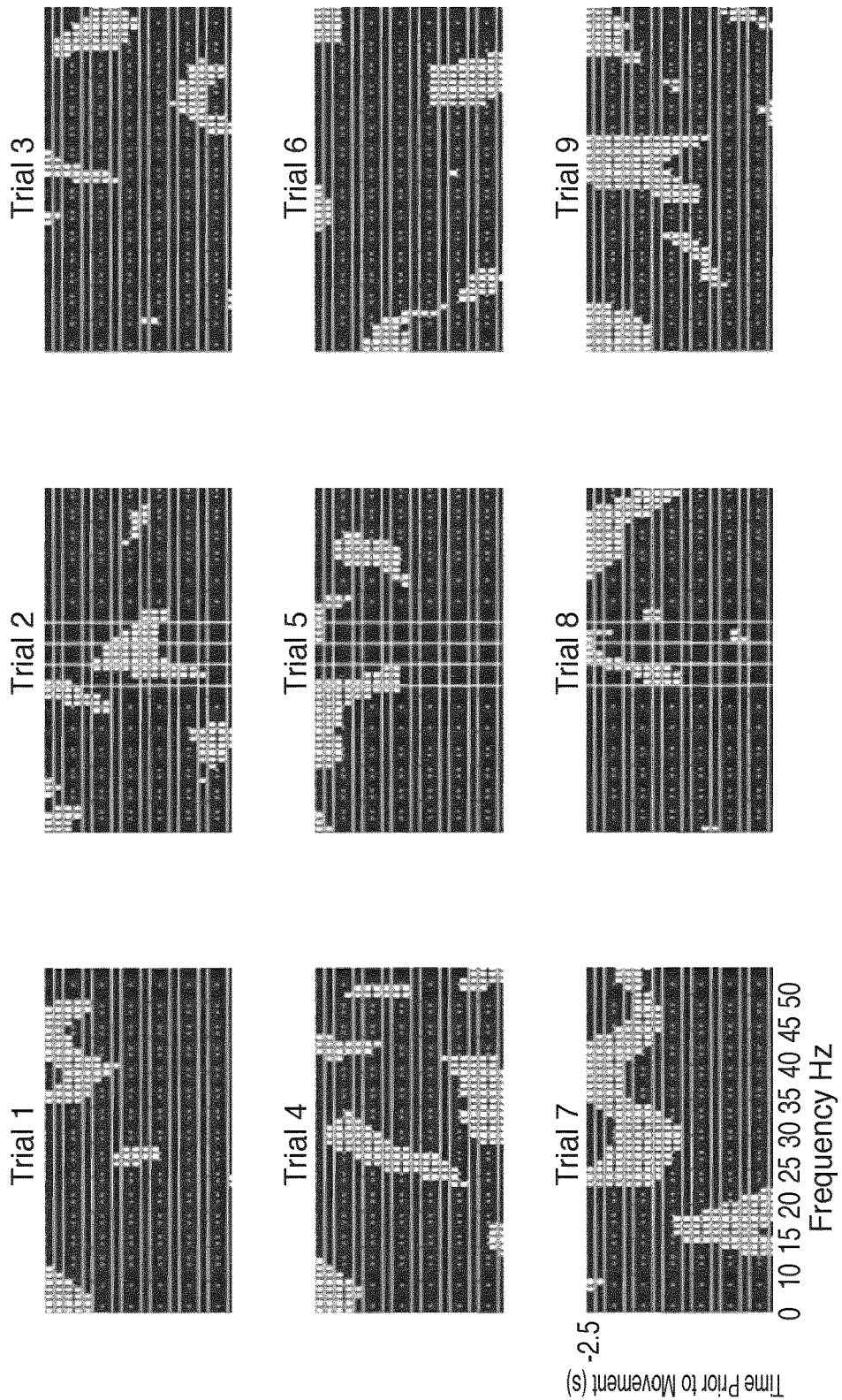
FIG. 11 provides exemplary tables for nine trials of a pinch grasp movement showing time and frequency elements in which the cross-correlation exceeded a threshold.

FIG. 11 shows the distribution of significant cross-correlations (r>0.8 and p<0.05) for the first nine trials of the pinch grasp and synthetic ERD signals, when the thresholding process is applied to the EEG activity recorded at C3 from one participant. The areas in white represent the times prior to the onset of movement when the correlation between each time-resolved frequency signal and the synthetic ERD exceeded the threshold value, such as 0.8, while the areas in black represent a correlation value less than the threshold value. This process was completed for each trial using every threshold value specified. Predictably, lower threshold values resulted in increased areas of white, while higher threshold values contain less areas of white.

Figure 12:
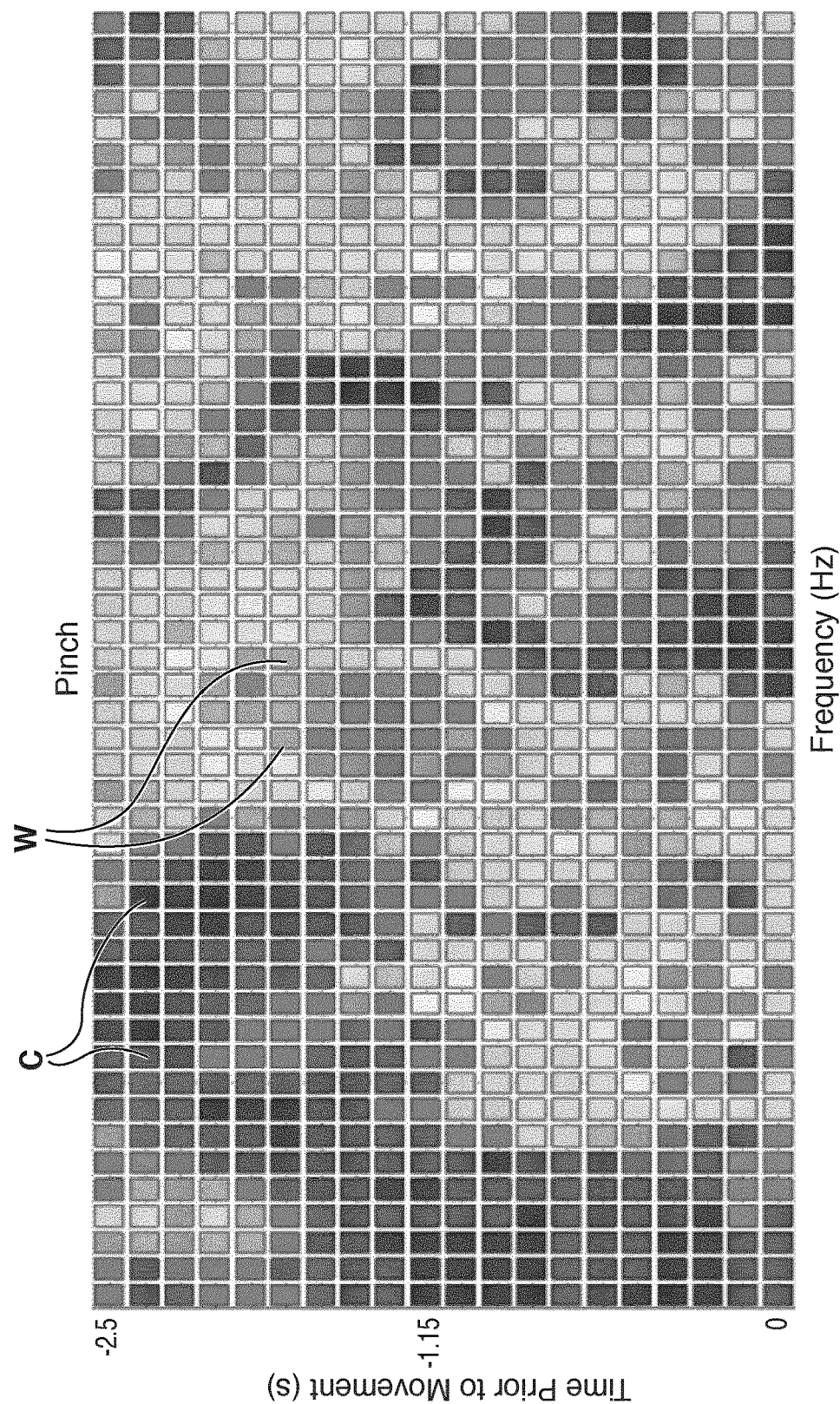
FIG. 12 shows a histogram illustrating the average of all correlation data for 30 trials of the pinch grasp movement of FIG. 12.

For each grasp, an average was calculated for each location in the matrix (step 108). FIG. 12 shows the "all-in" template with the averages of all correlation data above a threshold of 0.8 for 30 trials of the pinch grasp recorded from the F3 position ('all-in' template). Warmer colors (W) represent a higher incidence of significantly correlated area, and cooler colors (C) represent a lower incidence of significant correlations. (As used herein, 'all-in' templates are so named as they include every trial in the average.)

Figure 13:
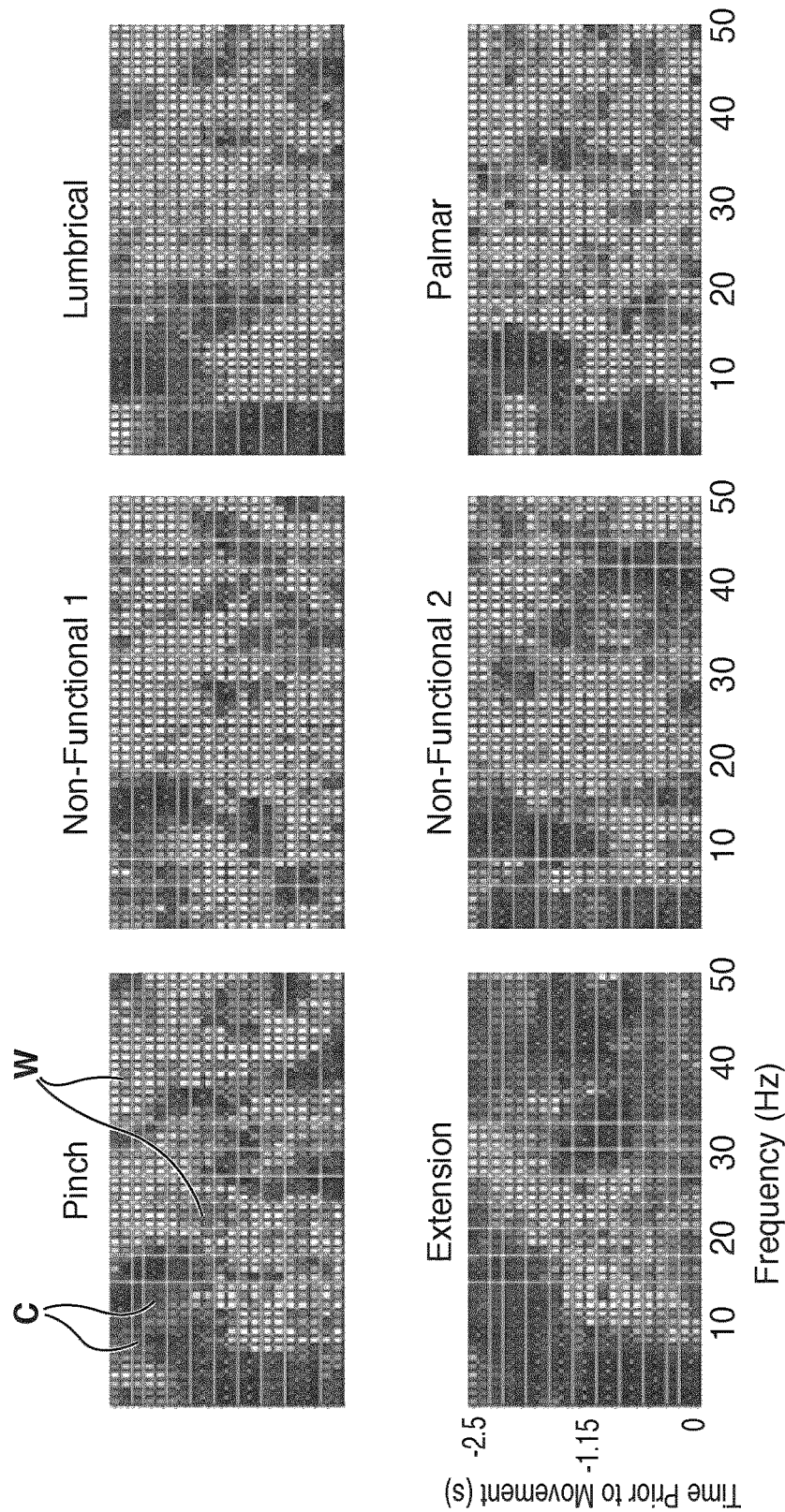
FIG. 13 shows exemplary histograms ('all-in' templates) of trials for six exemplary movements.

For a single electrode site, each participant had six 'all-in' templates (one for each hand movement), as shown in FIG. 13; resulting in a total of 42 'all-in' templates. In FIG. 13, warmer colors (W) represent a higher incidence of significantly correlated area, and cooler colors (C) represent a lower incidence of significant correlations. Next, 'one-out' templates were created by iteratively eliminating one trial and calculating the average of the remaining trials; for a grasp executed 30 times, 29 'one-out' templates; represented by 20×50×29 (time instances-frequency-trial number) tensors were generated for each threshold value.

The afore-mentioned process may be used to classify brain activity signals according to specific behaviours. This can be achieved by generating a set of templates by repeating steps 100 through 108 over several trials under the same behaviour and accumulating the results of all trials in a single histogram. This process is repeated for each one of the behaviours to be classified, and the templates are stored in template database 24. It is also possible to compare the magnitude of the elements in the histogram against a threshold and keep those (or a designated sample thereof) which exceed the threshold either in their actual magnitudes or normalized (set to one).

A new brain activity signal may be classified by applying steps 100 through 108 and, for a distance based classifier, the distance (Euclidean or any other suitable definition) between the correlation histogram (step 108) for the data to classify and each one of the correlation matrices for each one of the explored behaviours may be measured. An exemplified approach is described in more detail below.

The Euclidean distance between an 'all-in' template for a particular movement (FIG. 12) and an individual trial (FIG. 11) of a different (uncharacterized) movement may be used as a measure of the similarity between the two movements. For example, using data from a single electrode site and correlation threshold, the distance between the first trial of the pinch grasp (grasp 1) and the average of all trials of the non-functional 1 movement (grasp 2), may be calculated with the following equation:

$$D(\Lambda i, \Lambda j)_{1,2} = \left| G(i, j, 1)_1 - \frac{\left(\sum_{k=1}^{N_{NF1}} G(i, j, k)_2\right)}{N_{NF1}} \right|; \quad \text{(Equation 4.4)}$$

$i \in [1, \ldots, 20], j \in [1, \ldots, 50]$, and $N_{NF1}$ = the number of trials the non functional 1 movement was executed where $D(\Lambda i, \Lambda j)_{1,2}$ is a matrix containing numerical values of distance between each element of the first trial of the pinch grasp, $G(i,j,1)_1$, and the average of all trials of the non-functional 1 movement. Equation 4.4 is then applied to the first trial of the pinch grasp and every 'all-in' average of the remaining four movements which include: the lumbrical grasp, finger extension, the non-functional 2 movement, and palmar grasp. When comparing an individual trial with the template of the same movement, a 'one-out' template is used such that the individual trial being classified is not included in the average used to create the 'one-out' template.

For example, in the earlier described experimental protocol, the following equation was used when calculating the distance between Trial 1 of the pinch grasp and the average of trials of this movement:

$$D(\Lambda i, \Lambda j)_{1,1} = \left| G(i, j, 1)_1 - \frac{\left(\sum_{k=2}^{N_{Pinch}} G(i, j, k)_1\right)}{N_{Pinch}} \right|; \quad \text{(Equation 4.5)}$$

$i \in [1, \ldots, 20], j \in [1, \ldots, 50]$, and $N_{Pinch}$ = the number of trials the pinch grasp was executed where $D(\Lambda i, \Lambda j)_{1,1}$ is a matrix containing numerical values of distance between each element of the first trial of the pinch grasp ($G(i,j,1)$), and average of all trials of that movement ($G(i,j,k)_1$) with Trial 1 removed. The results of equations 4.4 and 4.5 were assembled in a 20×50×6 tensor containing numerical distances between Trial 1 of the pinch grasp and all other movements. Next, this tensor was summed along the $2^{nd}$ dimension (which refers to the frequencies included in the analysis: 1-50 Hz), resulting in a 20×6 matrix. The minimum non-zero value at each time instance was then identified and assigned a value of 1 and all other entries given a value of 0. For example, Table 2 illustrates the actual values of distance calculated between Trial 1 of the pinch grasp and the 'all-in' template of each additional grasp (columns 3-7 of Table 2) and between Trial 1 of the pinch grasp and the 'one-out' template of the pinch grasp (column 2 of Table 2) at each time interval prior to movement. Table 3 represents the binary version of the data, where values exceeding the minimum distance in each row is assigned a value of 1, and all other distances are given a value of 0.

Zero values in the table shown in Table 3 are excluded from the calculation of the minimum entry as these instances indicate the subtraction of two zero values, meaning that neither instance resulted in a value of correlation with the synthetic ERD above the set threshold (Equation 4.3). Entries of 1 in the column labeled 'Pinch' (highlighted) indicate time intervals when Trial 1 of pinch had a minimum distance from the average for the pinch grasp relative to the average of the remaining grasps.

Figure 14:
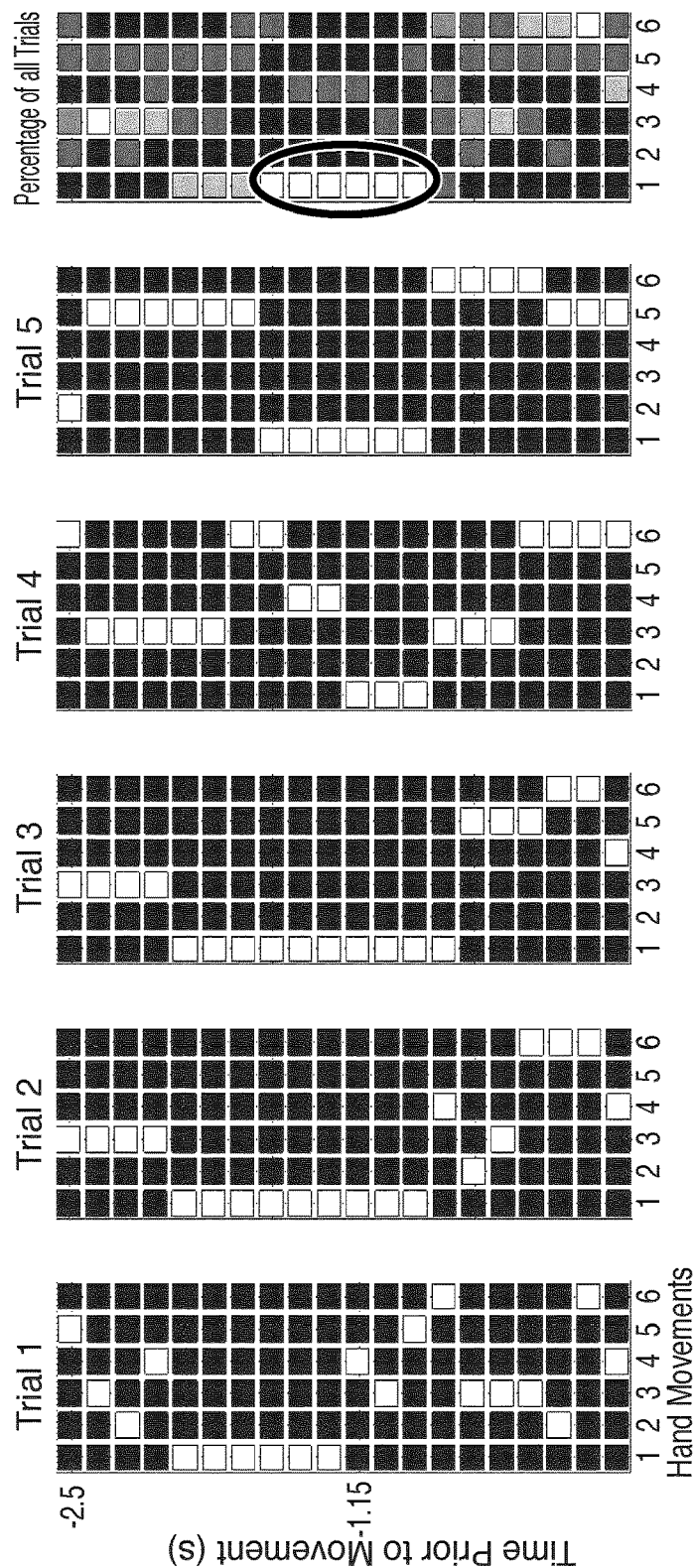
FIG. 14 illustrates the process described by tables of FIGS. 15 and 16 for the first five trials of the pinch grasp.

This process was then applied to every trial of the pinch grasp, resulting in $N_{Pinch}$×20×6 matrices. The percentage of all pinch grasp trials which were identified as having the minimum distance from the pinch grasp were then calculated. FIG. 14 illustrates the process described by Tables 2 and 3 for the first five trials of the pinch grasp, in which the areas in white represent the movement which had the minimum distance between Trial 1 of the pinch grasp at each time interval. The percentage of all pinch trials in which each of the six movements were identified to have the minimum distance is shown in FIG. 14. The areas of lighter color refer to a higher percentage of pinch trials with a minimum distance from a movement, and areas of darker color represent a lower percentage. Finally, the movement which contained the maximum percentage across all time intervals was selected to classify the movement. In the example illustrated by FIG. 14, the maximum percentage is indicated by an ellipse; occurring in the first column, which is designated to the pinch grasp, during the time interval of 1.56 to 0.88 seconds prior to the onset of movement with a maximum value of 71%. In other words, for this participant, the pinch grasp is classified correctly in 71% of trials using this particular electrode and correlation threshold during this specified time interval. To complete the classification for the pinch grasp, the same procedure described in this section was repeated for every electrode site (C1, C2, C3, C4, CZ, F3, F4, and FZ) and every value of correlation threshold (0.60, 0.65, 0.70, 0.75, 0.80, 0.85, and 0.90) resulting in 56 matrices (8 electrode sites×7 threshold values). Ultimately, the highest percentage of classification achieved across any of the 56 matrices is selected to classify the movement. The remaining movements were classified using the same procedure.

Figure 15:
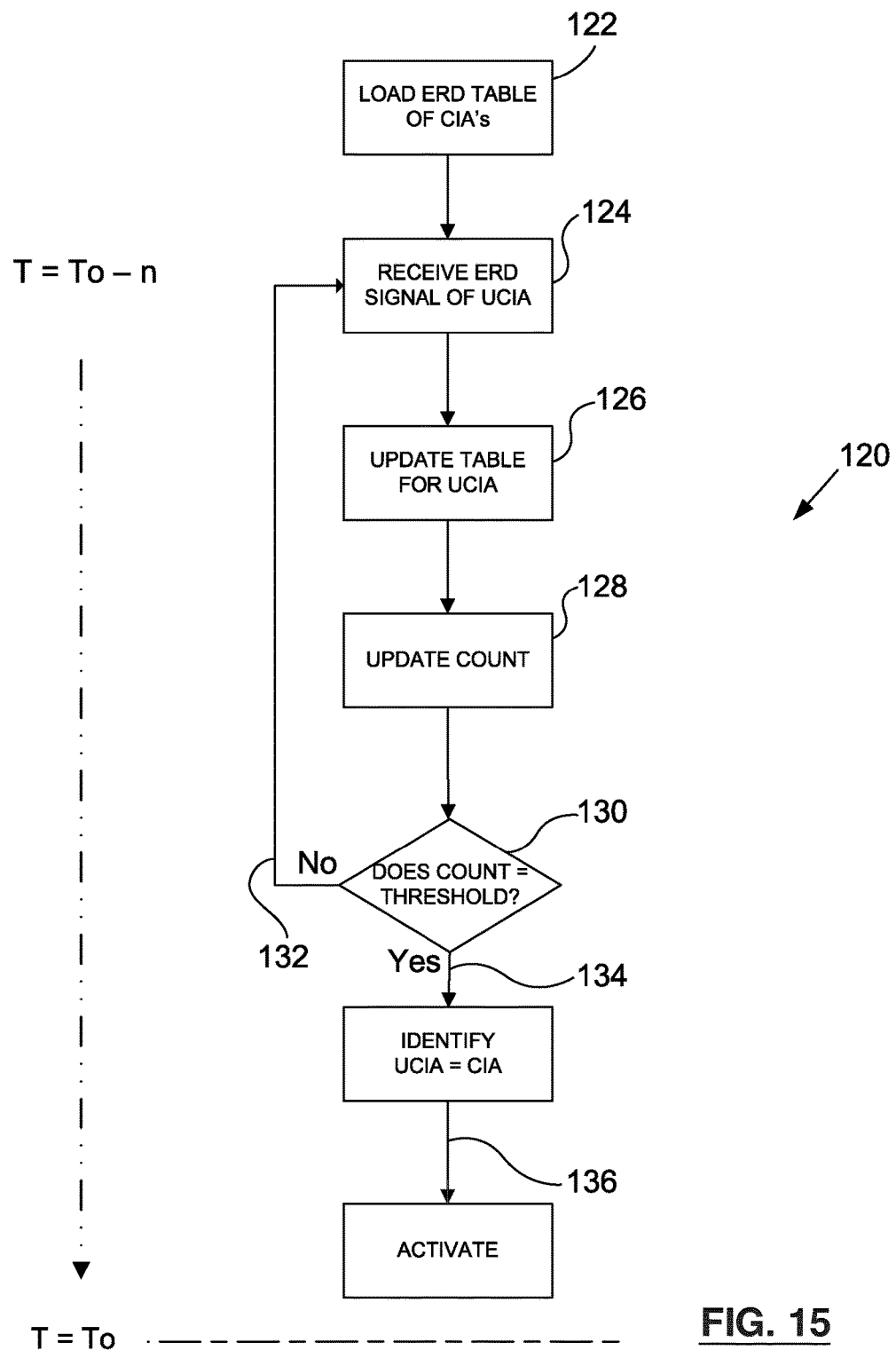
FIG. 15 illustrates an exemplary method for characterizing an ERD signal.

FIG. 15 illustrates an exemplary embodiment of a method 120 for characterizing a brain activity signal corresponding to an intended activity (IA). In this case the method steps are carried out in advance of T=To, that is the time signifying the initiation of a motor event, following the IA. First, at 122, an ERD table is accessed for a number of characterized intended activities (CIA's), following from one or more of the exemplified methods or protocols mentioned herein.

Next, at 124, at a given T=T1, an ERD signal is recorded for an uncharacterized intended activity (UCIA). At step 126, an ERD table is updated for the UCIA for T1. At 128, a correlation count for each CIA is advanced when a minimum distance is recorded between corresponding segments of the ERD tables of the CIA's and the UCIA. Next, at 130, all the correlation counts are compared against a predetermined minimum count threshold, and if no count exceeds the threshold, then at 132, the ERD signal is received for the next time increment. If any one count exceeds the threshold, then at 134 the UCIA is determined to be the CIA corresponding to the threshold-exceeding count, and at 136, an activation signal is issued, before T=To.

The steps 132, 136 and 136 may be carried out in real time, that is in the time period of the pre-motor activity, that is between the instant the IA signal is received and the instant at which the action corresponding to the IA is to be carried out. This means that the actual processing needed between receipt of the IA signal and the activation signal may vary from one received ERD signal to the next, depending on the nature of the IA. For instance, an ERD signal for moving a finger in a 90 degree path, in system that is capable of detecting the difference between a 90 degree movement and a 45 degree movement, may require more time intervals to achieve the minimum correlation as the system is evaluating very slight differences in the ERD signals for both. In contrast, if the system is only capable of recording a finger per se and not sufficiently granular to distinction different finger movements may achieve a minimum correlation count in a relatively shorter time period, when it is distinguishing between, for instance, finger movements versus write movements. Still further, the steps may be carried out in batch format, that is they may be carried for a given number of time intervals, which may be set to remain constant from one analysis to the next.

Since the EEG data used for movement classification was limited to only pre-motor activity, exemplified embodiments may be used to both differentiate and predict the hand movement to be performed with reasonable accuracy.

In exemplary embodiments, analysis required for classification of each trial may be applied only to the EEG data recorded prior to the intended activity (IA), such as a hand movement by the participant. The pre-movement interval may range from 2.5 seconds to 0 seconds prior to movement and may be segmented into a number of discrete time steps, such as 20 in the above example. The percentage of trials classified for each of the six movements may be evaluated at each time step, and the highest percentage may then be selected to classify the movement. In some cases, an intended activity may be observed as early as 1.5 seconds prior to movement, though processing speeds in an online, synchronous, BCI and FES application may, in cases with suitable processing speeds, such as in the vicinity of 0.3 s or less, an exemplified method may be configured to detect and classify an ERD signal in time to trigger an appropriate response via FES. As a result, exemplified methods and systems herein may be deployed to stimulate a volitional hand movement in the operator for the purposes of motor training; as discussed earlier, this approach may be successful in restoring motor control of the hand in stroke patients with hemiplegia. In other words, exemplified methods and systems herein may be configured to characterize an intended activity and trigger an action to an FES treatment step or another action in a user device in a real or virtual environment at or near an optimal firing time, as can be configured according to conditions appropriate for the application. Thus, exemplified methods and systems may be configured so that a time duration between an action signal and the expiry of the pre-motor phase of the associated action, is minimized and/or optimized, according to such factors as operational delays, as may occur in prosthetic, orthotic, exoskeletal, robotic or other automated devices and the like, which may be configured to carry out a representation of, or for that matter operationally mimic, an intended action. For instance, some devices may require a period of latency for preparation to a ready state in advance of action. Further, some users may encounter operational delays arising from some brain function limiting conditions.

For instance, a BCI may be implemented as a "brain-switch" to produce a user device instruction by way of one or more control signal, which may be conveyed to the user device to execute a prescribed action, along with additional information in relation to the prescribed action, such as coordinates for the placement of a prosthetic appendage in a target configuration.

In the above exemplary protocol, the average time when each trial was successfully classified ranged from 0.3 seconds to 2 seconds prior to movement for the dominant hand; and 0.3 seconds to 1.4 seconds for non-dominant hand movements across participants. The ERD signal in some cases was observed and the intended activity classified as early 1.5 seconds prior to movement, and in one example was detected in real-time an average of 0.62 seconds before movement. In the above exemplary protocol, a maximum of eight EEG electrodes was used, which may be substantially less than other prior methods which may require substantially more electrodes and are not adaptable to classify different hand movements using pre-motor activity. As such, the use of the eight EEG electrodes, makes it more viable for use in a clinical setting. That said, in some exemplary embodiments, operable results may be achieved with data from a single electrode.

In exemplary embodiments, a set of parameters may be selected which may be unique for each participant, or for a group of participants, depending on such variables including the type of hand movement, and the spatial location of electrodes. In yet another exemplary embodiment, methods and systems described above may be employed to create non-invasive brain-computer interfaces with high communication throughputs (each identifiable behaviour represents a different command available to the user).

In yet another exemplary embodiment, methods and systems described above may be employed to create brain-computer interfaces with a high level of interaction transparency if used to control a device to facilitate movement of a paralyzed or nonexistent limb (e.g., a functional electrical stimulator).

In yet another exemplary embodiment, methods and systems described above may be employed to enhance therapies which facilitate a movement of a paralyzed limb using artificial/external means, such as functional electrical stimulation therapy, after patients attempt the movement for several seconds. For example, the afore-mentioned methods and systems may improve these therapies by 1) triggering the mechanism to produce the movement by identifying the intention to move through analysis of brain signals alone, 2) facilitating the specific intended movement, 3) providing a mechanism to ensure that patients are in fact attempting to move, and 4) triggering the mechanism to produce movement within physiologically realistic latencies.

In yet another exemplary embodiment, the afore-mentioned methods and systems may be employed to image brain activities, for example, by conducting analysis of neurological events of short duration which may lead to the discovery and characterization of new features correlated with behaviour and other neurophysiological events.

Accordingly, the afore-mentioned methods and system may be integrated into new or existing commercial software for the analysis of brain activities.

In yet another exemplary embodiment, the afore-mentioned methods and systems may be employed as screening and/or diagnostic tools for neurological conditions based on the ability to identify transient events in electroencephalographic (and potentially electrocorticographic) signals. Accordingly, the afore-mentioned methods and systems may be integrated into new or existing commercial software for the analysis of brain activities.

In yet another exemplary embodiment, the afore-mentioned methods and systems may be employed to create access methods for patients that are unable to use current assistive devices reliably. The resulting assistive technologies may have a high degree of transparency if the intended and executed actions correspond exactly or at least operatively, and/or may offer a number of options greater than what it is currently possible.

In yet another exemplary embodiment, the brain activity signal may be an electrocorticographic (ECoG) signal.

Although the above-noted methods and systems have been described in terms of humans, these methods and systems are applicable to animals.

Thus, exemplary embodiments provide technical utility by providing a technical solution to the conventional technical problem of identifying an IA, and in some cases a series of IA's in succession, in a quantifiable way, from one or more raw analog signals obtained from an electrode array, in a reasonably timely and accurate manner, to enable effective control of several external (e.g., virtual or real) actions in a synchronous manner to the actions to be taken as a result of the identified IA or IA's. Furthermore, in some exemplary embodiments, the provided technical solution may be to the problem of identifying the IA, and in some cases a series of IA's in succession from a single electrode, rather than an array of electrodes.

Thus, some exemplary embodiments utilize a special purpose computer for this purpose, acting in a quantifiable and repeatable manner to translate raw analog signals into quantifiable, identifiable and/or mappable IA's so as to enable control of an action device according to the quantifiable, identifiable and/or mappable IA's. Accordingly, the presently disclosed embodiments provide technical utility by enabling issuance of quantifiable, identifiable and mappable instructions to a prosthetic, neuroprosthetic, FES, robot, orthotic device, or to a virtual device.

The preceding detailed description of exemplary embodiments of the invention makes reference to the accompanying drawings, which show the exemplary embodiment by way of illustration. While these exemplary embodiments are described in sufficient detail to enable those skilled in the art to practice the invention, it should be understood that other embodiments may be realized and that logical and mechanical changes may be made without departing from the spirit and scope of the invention. For example, the steps recited in any of the method or process claims may be executed in any order and are not limited to the order presented. Further, the present invention may be practiced using one or more servers, as necessary. Thus, the preceding detailed description is presented for purposes of illustration only and not of limitation, and the scope of the invention is defined by the preceding description, and with respect to the attached claims.

TABLE 1

| Interval Number | Interval Start | Interval End | Mid-Point |
|---|---|---|---|
| 1 | −3.87 | −1.15 | −2.51 |
| 2 | −3.74 | −1.02 | −2.38 |
| 3 | −3.60 | −0.88 | −2.24 |
| 4 | −3.46 | −0.74 | −2.10 |
| 5 | −3.33 | −0.61 | −1.97 |
| 6 | −3.19 | −0.47 | −1.83 |
| 7 | −3.06 | −0.34 | −1.70 |
| 8 | −2.92 | −0.20 | −1.56 |
| 9 | −2.78 | −0.06 | −1.42 |
| 10 | −2.65 | 0.07 | −1.29 |
| 11 | −2.51 | 0.21 | −1.15 |
| 12 | −2.38 | 0.34 | −1.02 |
| 13 | −2.24 | 0.48 | −0.88 |
| 14 | −2.10 | 0.62 | −0.74 |
| 15 | −1.97 | 0.75 | −0.61 |
| 16 | −1.83 | 0.89 | −0.47 |
| 17 | −1.70 | 1.02 | −0.34 |
| 18 | −1.56 | 1.16 | −0.20 |
| 19 | −1.42 | 1.30 | −0.06 |
| 20 | −1.29 | 1.43 | 0.07 |

TABLE 2

| Time Prior to Movement | Pinch | Non-Functional 1 | Lumbrical | Extension | Non-Functional 2 | Palmar |
|---|---|---|---|---|---|---|
| −2.51 | 0.03 | 0.19 | 0.06 | 0.06 | 0.10 | 0.55 |
| −2.38 | 0.06 | 0.13 | 0.13 | 0.48 | 0.10 | 0.10 |
| −2.24 | 0.48 | 0.16 | 0.03 | 0.06 | 0.10 | 0.16 |
| −2.10 | 0.03 | 0.16 | 0.06 | 0.61 | 0.06 | 0.06 |
| −1.97 | 0.10 | 0.06 | 0.10 | 0.65 | 0.06 | 0.03 |
| −1.83 | 0.06 | 0.00 | 0.65 | 0.13 | 0.07 | 0.10 |
| −1.70 | 0.03 | 0.13 | 0.00 | 0.71 | 0.06 | 0.06 |
| −1.56 | 0.13 | 0.13 | 0.03 | 0.10 | 0.00 | 0.61 |
| −1.42 | 0.00 | 0.06 | 0.13 | 0.68 | 0.10 | 0.03 |
| −1.29 | 0.10 | 0.10 | 0.03 | 0.10 | 0.06 | 0.61 |
| −1.15 | 0.68 | 0.03 | 0.00 | 0.06 | 0.06 | 0.16 |
| −1.02 | 0.71 | 0.06 | 0.06 | 0.06 | 0.06 | 0.03 |
| −0.88 | 0.77 | 0.00 | 0.10 | 0.03 | 0.06 | 0.03 |
| −0.74 | 0.06 | 0.03 | 0.16 | 0.71 | 0.03 | 0.00 |
| −0.61 | 0.13 | 0.77 | 0.03 | 0.06 | 0.00 | 0.00 |
| −0.47 | 0.03 | 0.84 | 0.06 | 0.06 | 0.00 | 0.00 |
| −0.34 | 0.00 | 0.03 | 0.04 | 0.84 | 0.06 | 0.04 |
| −0.20 | 0.06 | 0.74 | 0.03 | 0.10 | 0.07 | 0.00 |
| −0.06 | 0.68 | 0.13 | 0.10 | 0.03 | 0.04 | 0.04 |
| 0.07 | 0.55 | 0.06 | 0.19 | 0.07 | 0.13 | 0.00 |

TABLE 3

| Time Prior to Movement | Pinch | Non-Functional 1 | Lumbrical | Extension | Non-Functional 2 | Palmar |
|---|---|---|---|---|---|---|
| −2.51 | 1 | 0 | 0 | 0 | 0 | 0 |
| −2.38 | 1 | 0 | 0 | 0 | 0 | 0 |
| −2.24 | 0 | 0 | 1 | 0 | 0 | 0 |
| −2.10 | 1 | 0 | 0 | 0 | 0 | 0 |
| −1.97 | 0 | 0 | 0 | 0 | 0 | 1 |
| −1.83 | 1 | 0 | 0 | 0 | 0 | 0 |
| −1.70 | 1 | 0 | 0 | 0 | 0 | 0 |
| −1.56 | 0 | 0 | 1 | 0 | 0 | 0 |
| −1.42 | 0 | 0 | 0 | 0 | 0 | 1 |
| −1.29 | 0 | 0 | 1 | 0 | 0 | 0 |
| −1.15 | 0 | 1 | 0 | 0 | 0 | 0 |
| −1.02 | 0 | 0 | 0 | 0 | 0 | 1 |
| −0.88 | 0 | 0 | 0 | 0 | 0 | 1 |
| −0.74 | 0 | 1 | 0 | 0 | 0 | 0 |
| −0.61 | 0 | 0 | 1 | 0 | 0 | 0 |
| −0.47 | 1 | 0 | 0 | 0 | 0 | 0 |
| −0.34 | 0 | 1 | 0 | 0 | 0 | 0 |
| −0.20 | 1 | 0 | 0 | 0 | 0 | 0 |

TABLE 3-continued

| Time Prior to Movement | Pinch | Non-Func-tional 1 | Lumbrical | Extension | Non-Func-tional 2 | Palmar |
|---|---|---|---|---|---|---|
| −0.06 | 0 | 0 | 0 | 1 | 0 | 0 |
| 0.07 | 0 | 1 | 0 | 0 | 0 | 0 |

The invention claimed is:

1. A system for translating analog event-related desynchronization (ERD) signals from a user into an identifiable intended activity (IA), the system comprising:
   a. at least one input to receive one or more ERD signals;
   b. at least one output to send device action instructions to a user device to carry out a device action corresponding to the IA; and
   c. a controller to communicate with the at least one input and the at least one output of the user device, the controller including at least one special purpose processor configured to run at least one computer program:
      i. to record an ERD signal received from the at least one input, the ERD signal corresponding to an uncharacterized IA of the user for each time value of one or more successive time values,
      ii. for each time value:
         1. to access one or more ERD templates of coefficients for one or more characterized IA's, the ERD templates of coefficients being formed by correlating a plurality of time resolved frequency ERD signal values with a function approximating a synthetic ERD signal;
         2. to update an ERD table for the uncharacterized IA and to compare the updated ERD table with the ERD templates to determine whether the uncharacterized IA is an instance of one of the characterized IA's; and
      iii. to initiate a corresponding device action instruction on at the at least one output after a minimum number of time values necessary to determine whether the uncharacterized IA is an instance of one of the characterized IA's.

2. The system of claim 1, wherein the at least one computer program is configured to identify the IA in response to achievement of a predetermined correlation count, wherein each count corresponds to a correlation between corresponding segments of the ERD templates of the characterized IA's and the updated ERD table of the uncharacterized IA.

3. The system of claim 2, wherein the at least one computer program is configured to advance the correlation count in response to a minimum distance being recorded between corresponding segments of the ERD templates and updated ERD table of the characterized IA's and the uncharacterized IA respectively.

4. The system of claim 1, further comprising the user device, wherein the user device includes a robotic arm or device, a full or partial limb prosthesis, an orthotic device, an electrical stimulation device, or an interface to a virtual device.

5. The system of claim 1, wherein the at least one computer program is configured to initiate the device action instruction before the expiry of a pre-motor phase of a user action corresponding to the IA.

6. The system of claim 1, wherein the ERD signal is an electroencephalographic (EEG) or an electrocorticographic (ECoG) signal, a magnetic signal, or a chemical signal.

7. The system of claim 1, wherein the at least one input includes a single electrode.

8. A method for translating analog event-related desynchronization (ERD) signals from a user into an identifiable intended activity (IA) to form one or more ERD templates for use in associating an updated ERD table of an uncharacterized IA therewith to identify and initiate a corresponding intended device action by a user device, the method comprising:
   a. recording one or more ERD signals from one or more electrodes operatively placed on the user, wherein each of the ERD signals corresponds to a characterized intended activity (IA) of the user for each time value of one or more successive time values;
   b. for each time value, forming a temporo-spectral decomposition of the ERD signal, to form a plurality of time resolved frequency ERD signal values;
   c. associating each ERD signal value with a function approximating a synthetic ERD signal to form at least one ERD table of coefficients collectively representative of the characterized IA;
   d. repeating step c for a number of instances of the characterized IA to form a number of at least one ERD tables; and
   e. forming the ERD template for the characterized IA from the number of ERD tables for the characterized IA.

9. The method of claim 8, wherein the recording of the one or more ERD signals includes collecting one or more electrode signals from one or more electrodes, with one or more of the ERD tables being associated with a corresponding electrode signal.

10. The method of claim 8, wherein the time values correspond to overlapping or non-overlapping time intervals.

11. The method of claim 8, further comprising:
    a. recording the ERD signal corresponding to an uncharacterized IA for a number of successive time values and updating an ERD table for the uncharacterized IA for each time value; and
    b. associating the updated ERD table for the uncharacterized IA with the ERD template of the characterized IA to determine whether the uncharacterized IA is an instance of the characterized IA.

12. The method of claim 11, further comprising issuing a device action instruction after a minimum number of time values necessary to determine whether the uncharacterized IA is an instance of the characterized IA.

13. The method of claim 12, further comprising affirming that the uncharacterized IA is an instance of one of the characterized IA's in response to achievement of a predetermined correlation count, wherein each count corresponding to a correlation between corresponding segments of the updated ERD table of the uncharacterized IA and the ERD template of the characterized IA.

14. The method of claim 13, further comprising advancing the correlation count in response to a minimum distance being recorded between corresponding segments of the updated ERD table and the ERD template.

15. The method of claim 14, wherein the device action instruction occurs before an expiry of a pre-motor phase of an action corresponding to the affirmed IA.

16. The method of claim 15, wherein the time duration between the device action instruction and the expiry of the pre-motor phase, is minimized and/or optimized.

17. The method of claim 16, wherein the user device is one of a robotic arm or device, full limb prosthesis, partial limb prosthesis, or a user treatment device, a neuroprosthesis or functional electrical stimulation (FES) device that actuates a paralyzed limb, an orthotic device, or a virtual activity device.

\* \* \* \* \*